(12) United States Patent
Patangay et al.

(10) Patent No.: US 8,108,034 B2
(45) Date of Patent: Jan. 31, 2012

(54) SYSTEMS AND METHODS FOR VALVULAR REGURGITATION DETECTION

(75) Inventors: Abhilash Patangay, Little Canada, MN (US); Krzysztof Z. Siejko, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1524 days.

(21) Appl. No.: 11/287,978

(22) Filed: Nov. 28, 2005

(65) Prior Publication Data
US 2007/0123943 A1 May 31, 2007

(51) Int. Cl.
*A61N 1/00* (2006.01)
(52) U.S. Cl. ................. 600/509; 607/9; 607/17
(58) Field of Classification Search .......... 600/17, 600/509; 607/17, 9
See application file for complete search history.

(56) References Cited

U.S. PATENT DOCUMENTS

| | | | |
|---|---|---|---|
| 4,094,308 A | 6/1978 | Cormier | |
| 4,220,160 A | 9/1980 | Kimball et al. | |
| 4,289,141 A | 9/1981 | Cormier | |
| 4,354,497 A | 10/1982 | Kahn | |
| 4,428,378 A | 1/1984 | Anderson et al. | |
| 4,428,380 A | 1/1984 | Wong et al. | |
| 4,446,872 A | 5/1984 | Marsoner et al. | |
| 4,519,395 A | 5/1985 | Hrushesky | |
| 4,548,204 A | 10/1985 | Groch et al. | |
| 4,549,548 A | 10/1985 | Wittkampf et al. | |
| 4,554,922 A | 11/1985 | Prystowsky et al. | |
| 4,586,514 A | 5/1986 | Schlager et al. | |
| 4,628,934 A | 12/1986 | Pohndorf et al. | |
| 4,628,939 A | 12/1986 | Little et al. | |
| 4,649,930 A | 3/1987 | Groch et al. | |
| 4,674,518 A | 6/1987 | Salo | |
| 4,686,987 A | 8/1987 | Salo et al. | |
| 4,702,253 A | 10/1987 | Nappholz et al. | |
| 4,712,179 A | 12/1987 | Heimer | |
| 4,763,646 A | 8/1988 | Lekholm | |
| 4,773,401 A | 9/1988 | Citak et al. | |
| 4,777,960 A | 10/1988 | Berger et al. | |
| 4,796,639 A | 1/1989 | Snow et al. | |
| 4,809,697 A | 3/1989 | Causey, III et al. | |

(Continued)

FOREIGN PATENT DOCUMENTS

EP 297675 A1 1/1989

(Continued)

OTHER PUBLICATIONS

PCT/US00/17699, Jan. 18, 2001, Ferek-Petric, Bozidar.

(Continued)

*Primary Examiner* — Niketa Patel
*Assistant Examiner* — Alyssa M Alter
(74) *Attorney, Agent, or Firm* — Schwegman, Lundberg & Woessner, P.A.

(57) ABSTRACT

A system comprising an implantable medical device (IMD). The IMD includes an implantable sensor operable to produce an electrical signal representative of mechanical activity of a heart of a subject and a controller circuit coupled to the sensor. The controller circuit includes a wavelet filter module and a valvular regurgitation (VR) calculation module. The wavelet filter module is configured to extract signal energy information from the electrical signal. The energy information includes variation of signal amplitude with frequency and time. The VR calculation module is configured to calculate a measurement of VR for one or more heartbeats using the energy information.

35 Claims, 8 Drawing Sheets

U.S. PATENT DOCUMENTS

| | | | |
|---|---|---|---|
| 4,825,869 A | 5/1989 | Sasmor et al. | |
| 4,834,710 A | 5/1989 | Fleck | |
| 4,872,459 A | 10/1989 | Pless et al. | |
| 4,880,005 A | 11/1989 | Pless et al. | |
| 4,905,706 A | 3/1990 | Duff et al. | |
| 4,915,113 A | 4/1990 | Holman | |
| 4,922,907 A | 5/1990 | Hedin et al. | |
| 4,928,688 A | 5/1990 | Mower | |
| 4,945,909 A | 8/1990 | Fearnot et al. | |
| 4,967,760 A | 11/1990 | Bennett et al. | |
| 4,981,139 A | 1/1991 | Pfohl | |
| 4,989,611 A | 2/1991 | Zanetti et al. | |
| 5,007,427 A | 4/1991 | Sukuki et al. | |
| 5,010,889 A | 4/1991 | Bredesen et al. | |
| 5,012,815 A | 5/1991 | Bennett, Jr. et al. | |
| 5,014,698 A | 5/1991 | Cohen | |
| 5,025,809 A | 6/1991 | Johnson et al. | |
| 5,058,605 A | 10/1991 | Slovak | |
| 5,072,458 A | 12/1991 | Suzuki | |
| 5,097,831 A | 3/1992 | Lekholm | |
| 5,111,818 A | 5/1992 | Suzuki et al. | |
| 5,113,869 A | 5/1992 | Nappholz et al. | |
| 5,137,019 A | 8/1992 | Pederson et al. | |
| 5,156,149 A | 10/1992 | Hudrlik | |
| 5,158,079 A | 10/1992 | Adams et al. | |
| 5,159,932 A | 11/1992 | Zanetti et al. | |
| 5,168,869 A | 12/1992 | Chirife | |
| 5,174,289 A | 12/1992 | Cohen | |
| 5,179,947 A | 1/1993 | Meyerson et al. | |
| 5,184,615 A | 2/1993 | Nappholz et al. | |
| 5,190,035 A | 3/1993 | Salo et al. | |
| 5,199,428 A | 4/1993 | Obel et al. | |
| 5,218,969 A | 6/1993 | Bredesen et al. | |
| 5,226,413 A | 7/1993 | Bennett et al. | |
| 5,233,985 A | 8/1993 | Hudrlik | |
| 5,251,626 A | 10/1993 | Nickolls et al. | |
| 5,267,560 A | 12/1993 | Cohen | |
| 5,282,838 A | 2/1994 | Hauser et al. | |
| 5,284,136 A | 2/1994 | Hauck et al. | |
| 5,292,341 A | 3/1994 | Snell | |
| 5,301,679 A | 4/1994 | Taylor | |
| 5,318,595 A | 6/1994 | Ferek-Petric et al. | |
| 5,321,618 A | 6/1994 | Gessman | |
| 5,330,511 A | 7/1994 | Boute | |
| 5,331,768 A | 7/1994 | Takeuchi | |
| 5,334,222 A | 8/1994 | Salo et al. | |
| 5,337,752 A | 8/1994 | Reeves | |
| 5,365,932 A | 11/1994 | Greenhut | |
| 5,370,665 A | 12/1994 | Hudrlik | |
| 5,372,607 A | 12/1994 | Stone et al. | |
| 5,391,190 A | 2/1995 | Pederson et al. | |
| 5,417,717 A | 5/1995 | Salo et al. | |
| 5,421,830 A | 6/1995 | Epstein et al. | |
| 5,472,453 A | 12/1995 | Alt | |
| 5,484,419 A | 1/1996 | Fleck | |
| 5,487,752 A | 1/1996 | Salo et al. | |
| 5,496,361 A | 3/1996 | Moberg et al. | |
| 5,514,161 A | 5/1996 | Limousin | |
| 5,514,163 A | 5/1996 | Markowitz et al. | |
| 5,527,347 A | 6/1996 | Shelton et al. | |
| 5,534,016 A | 7/1996 | Boute | |
| 5,540,727 A | 7/1996 | Tockman et al. | |
| 5,549,650 A | 8/1996 | Bornzin et al. | |
| 5,549,654 A | 8/1996 | Powell | |
| 5,554,177 A | 9/1996 | Kieval et al. | |
| 5,584,867 A | 12/1996 | Limousin et al. | |
| 5,584,868 A | 12/1996 | Salo et al. | |
| 5,593,431 A | 1/1997 | Sheldon | |
| 5,594,638 A | 1/1997 | Iliff | |
| 5,607,460 A | 3/1997 | Kroll et al. | |
| 5,609,612 A | 3/1997 | Plicchi et al. | |
| 5,626,620 A | 5/1997 | Kieval et al. | |
| 5,626,623 A | 5/1997 | Kieval et al. | |
| 5,628,777 A | 5/1997 | Moberg et al. | |
| 5,630,835 A | 5/1997 | Brownlee | |
| 5,674,256 A | 10/1997 | Carlson | |
| 5,674,259 A | 10/1997 | Gray | |
| 5,683,429 A | 11/1997 | Mehra | |
| 5,685,317 A | 11/1997 | Sjostrom | |
| 5,687,738 A | 11/1997 | Shapiro et al. | |
| 5,690,689 A | 11/1997 | Sholder | |
| 5,690,690 A | 11/1997 | Nappholz et al. | |
| 5,697,375 A | 12/1997 | Hickey | |
| 5,697,959 A | 12/1997 | Poore | |
| 5,700,283 A | 12/1997 | Salo | |
| 5,713,930 A | 2/1998 | van der Veen et al. | |
| 5,716,382 A | 2/1998 | Snell | |
| 5,716,383 A | 2/1998 | Kieval et al. | |
| 5,720,771 A | 2/1998 | Snell | |
| 5,722,999 A | 3/1998 | Snell | |
| 5,724,985 A | 3/1998 | Snell et al. | |
| 5,725,562 A | 3/1998 | Sheldon | |
| 5,749,906 A | 5/1998 | Kieval et al. | |
| 5,759,199 A | 6/1998 | Snell et al. | |
| 5,792,195 A | 8/1998 | Carlson et al. | |
| 5,792,203 A | 8/1998 | Schroeppel | |
| 5,797,970 A | 8/1998 | Pouvreau | |
| 5,800,471 A | 9/1998 | Baumann | |
| 5,800,473 A | 9/1998 | Faisandier | |
| 5,824,019 A | 10/1998 | Rueter et al. | |
| 5,833,623 A | 11/1998 | Mann et al. | |
| 5,836,987 A | 11/1998 | Baumann et al. | |
| 5,860,918 A | 1/1999 | Schradi et al. | |
| 5,860,933 A | 1/1999 | Don Michael | |
| 5,891,178 A | 4/1999 | Mann et al. | |
| 5,911,738 A | 6/1999 | Sikorski et al. | |
| 5,935,081 A | 8/1999 | Kadhiresan | |
| 5,935,160 A | 8/1999 | Auricchio et al. | |
| 5,987,352 A | 11/1999 | Klein et al. | |
| 5,991,661 A | 11/1999 | Park et al. | |
| 5,995,871 A | 11/1999 | Knisley | |
| 6,002,777 A | 12/1999 | Grasfield et al. | |
| 6,009,349 A | 12/1999 | Mouchawar et al. | |
| 6,015,388 A | 1/2000 | Sackner et al. | |
| 6,016,442 A | 1/2000 | Hsu et al. | |
| 6,021,350 A | 2/2000 | Mathson | |
| 6,022,322 A | 2/2000 | Prutchi | |
| 6,022,963 A | 2/2000 | McGall et al. | |
| 6,026,324 A | 2/2000 | Carlson | |
| 6,038,483 A | 3/2000 | KenKnight et al. | |
| 6,044,297 A | 3/2000 | Sheldon et al. | |
| 6,044,298 A | 3/2000 | Salo et al. | |
| 6,044,299 A | 3/2000 | Nilsson | |
| 6,045,513 A | 4/2000 | Stone et al. | |
| 6,053,872 A | 4/2000 | Mohler | |
| 6,058,329 A | 5/2000 | Salo et al. | |
| 6,064,910 A | 5/2000 | Andersson et al. | |
| 6,070,101 A | 5/2000 | Struble et al. | |
| 6,076,015 A | 6/2000 | Hartley et al. | |
| 6,077,227 A | 6/2000 | Miesel | |
| 6,091,990 A | 7/2000 | Hsu et al. | |
| 6,104,949 A | 8/2000 | Pitts Crick et al. | |
| 6,108,577 A | 8/2000 | Benser | |
| 6,112,117 A | 8/2000 | KenKnight et al. | |
| 6,115,628 A | 9/2000 | Stadler et al. | |
| 6,115,630 A | 9/2000 | Stadler et al. | |
| 6,128,526 A | 10/2000 | Stadler et al. | |
| 6,144,880 A | 11/2000 | Ding et al. | |
| 6,151,524 A | 11/2000 | Krig et al. | |
| 6,152,884 A | 11/2000 | Bjorgaas | |
| 6,152,955 A | 11/2000 | KenKnight et al. | |
| 6,161,042 A | 12/2000 | Hartley et al. | |
| 6,168,563 B1 | 1/2001 | Brown | |
| 6,190,324 B1 | 2/2001 | Kieval et al. | |
| 6,193,668 B1 | 2/2001 | Chassaing et al. | |
| 6,208,900 B1 | 3/2001 | Ecker et al. | |
| 6,208,901 B1 | 3/2001 | Hartung | |
| 6,223,082 B1 | 4/2001 | Bakels et al. | |
| 6,230,059 B1 | 5/2001 | Duffin | |
| 6,231,516 B1 | 5/2001 | Keilman et al. | |
| 6,236,882 B1 | 5/2001 | Lee et al. | |
| 6,240,317 B1 | 5/2001 | Villaseca et al. | |
| 6,251,126 B1 | 6/2001 | Ottenhoff et al. | |
| 6,264,611 B1 | 7/2001 | Ishikawa et al. | |
| 6,269,269 B1 | 7/2001 | Ottenhoff et al. | |
| 6,272,377 B1 | 8/2001 | Sweeney et al. | |
| 6,272,379 B1 | 8/2001 | Fischell et al. | |

| Patent Number | Date | Inventors |
|---|---|---|
| 6,273,856 B1 | 8/2001 | Sun et al. |
| 6,275,727 B1 | 8/2001 | Hopper et al. |
| 6,278,894 B1 | 8/2001 | Salo et al. |
| 6,280,389 B1 | 8/2001 | Ding et al. |
| 6,280,409 B1 | 8/2001 | Stone et al. |
| 6,285,898 B1 | 9/2001 | Ben-Haim |
| 6,285,907 B1 | 9/2001 | Kramer et al. |
| 6,298,269 B1 | 10/2001 | Sweeney |
| 6,304,773 B1 | 10/2001 | Taylor et al. |
| 6,311,089 B1 | 10/2001 | Mann et al. |
| 6,312,378 B1 | 11/2001 | Bardy |
| 6,314,323 B1 | 11/2001 | Ekwall et al. |
| 6,324,421 B1 | 11/2001 | Stadler et al. |
| 6,336,903 B1 | 1/2002 | Bardy |
| 6,347,245 B1 | 2/2002 | Lee et al. |
| 6,351,672 B1 | 2/2002 | Park et al. |
| 6,351,673 B1 | 2/2002 | Ding et al. |
| 6,351,675 B1 | 2/2002 | Tholen et al. |
| 6,360,127 B1 | 3/2002 | Ding et al. |
| 6,361,522 B1 | 3/2002 | Scheiner et al. |
| 6,363,279 B1 | 3/2002 | Ben-Haim et al. |
| 6,366,811 B1 | 4/2002 | Carlson |
| 6,368,283 B1 | 4/2002 | Xu et al. |
| 6,368,284 B1 | 4/2002 | Bardy |
| 6,370,424 B1 | 4/2002 | Prutchi |
| 6,381,493 B1 | 4/2002 | Stadler et al. |
| 6,383,136 B1 | 5/2002 | Jordan |
| 6,397,100 B2 | 5/2002 | Stadler et al. |
| 6,398,728 B1 | 6/2002 | Bardy |
| 6,409,675 B1 | 6/2002 | Turcott |
| 6,411,840 B1 | 6/2002 | Bardy |
| 6,411,847 B1 | 6/2002 | Mower |
| 6,415,033 B1 | 7/2002 | Halleck et al. |
| 6,430,439 B1 | 8/2002 | Wentkowski et al. |
| 6,438,407 B1 | 8/2002 | Ousdigian et al. |
| 6,438,421 B1 | 8/2002 | Stahmann et al. |
| 6,440,066 B1 | 8/2002 | Bardy |
| 6,440,082 B1 | 8/2002 | Joo et al. |
| 6,442,433 B1 | 8/2002 | Linberg |
| 6,445,953 B1 | 9/2002 | Bulkes et al. |
| 6,449,510 B1 | 9/2002 | Albers et al. |
| 6,459,929 B1 | 10/2002 | Hopper et al. |
| 6,466,821 B1 | 10/2002 | Pianca et al. |
| 6,477,402 B1 | 11/2002 | Lynch et al. |
| 6,477,406 B1 | 11/2002 | Turcott |
| 6,478,746 B2 | 11/2002 | Chassaing et al. |
| 6,480,733 B1 | 11/2002 | Turcott |
| 6,480,742 B2 | 11/2002 | Stahmann et al. |
| 6,491,639 B1 | 12/2002 | Turcott |
| 6,496,715 B1 | 12/2002 | Lee et al. |
| 6,496,721 B1 | 12/2002 | Yonce |
| 6,501,983 B1 | 12/2002 | Natarajan et al. |
| 6,507,756 B1 | 1/2003 | Heynen et al. |
| 6,512,952 B2 | 1/2003 | Stahmann et al. |
| 6,520,924 B2 | 2/2003 | Lee |
| 6,522,921 B2 | 2/2003 | Stahmann et al. |
| 6,522,923 B1 | 2/2003 | Turcott |
| 6,527,729 B1 | 3/2003 | Turcott |
| 6,531,907 B2 | 3/2003 | Dooley et al. |
| 6,542,775 B2 | 4/2003 | Ding et al. |
| 6,553,258 B2 | 4/2003 | Stahmann et al. |
| RE38,119 E | 5/2003 | Mower |
| 6,567,700 B1 | 5/2003 | Turcott et al. |
| 6,569,145 B1 | 5/2003 | Shmulewitz et al. |
| 6,575,916 B2 | 6/2003 | Halleck et al. |
| 6,584,362 B1 | 6/2003 | Scheiner et al. |
| 6,604,000 B2 | 8/2003 | Lu |
| 6,625,493 B2 | 9/2003 | Kroll et al. |
| 6,626,842 B2 | 9/2003 | Oka |
| 6,628,988 B2 | 9/2003 | Kramer et al. |
| 6,643,548 B1 | 11/2003 | Mai et al. |
| 6,650,940 B1 | 11/2003 | Zhu et al. |
| 6,658,292 B2 | 12/2003 | Kroll et al. |
| 6,665,564 B2 | 12/2003 | Lincoln et al. |
| 6,666,826 B2 | 12/2003 | Salo et al. |
| 6,684,103 B2 | 1/2004 | Ding et al. |
| 6,711,436 B1 | 3/2004 | Duhaylongsod |
| 6,719,701 B2 | 4/2004 | Lade |
| 6,733,464 B2 | 5/2004 | Olbrich et al. |
| 6,752,765 B1 | 6/2004 | Jensen et al. |
| 6,783,979 B2 | 8/2004 | Rosen et al. |
| 6,792,308 B2 | 9/2004 | Corbucci |
| 6,795,732 B2 | 9/2004 | Stadler et al. |
| 6,810,284 B1 | 10/2004 | Bradley |
| 6,810,287 B2 | 10/2004 | Zhu et al. |
| 6,816,744 B2 | 11/2004 | Garfield et al. |
| 6,824,519 B2 | 11/2004 | Narimatsu et al. |
| 6,827,690 B2 | 12/2004 | Bardy |
| 6,830,548 B2 | 12/2004 | Bonnet et al. |
| 6,842,642 B2 | 1/2005 | Vanhout |
| 6,845,263 B2 | 1/2005 | Kawaguchi |
| 6,849,611 B2 | 2/2005 | Rosen et al. |
| 6,865,420 B1 | 3/2005 | Kroll |
| 6,885,889 B2 | 4/2005 | Chinchoy |
| 6,907,285 B2 | 6/2005 | Denker et al. |
| 6,913,577 B2 | 7/2005 | Bardy |
| 6,915,160 B2 | 7/2005 | Auricchio et al. |
| 6,950,701 B2 | 9/2005 | Begemann et al. |
| 6,961,617 B2 | 11/2005 | Snell |
| 6,963,777 B2 | 11/2005 | Lincoln et al. |
| 6,980,851 B2 | 12/2005 | Zhu et al. |
| 7,010,342 B2 | 3/2006 | Galen et al. |
| 7,020,521 B1 | 3/2006 | Brewer et al. |
| 7,043,305 B2 | 5/2006 | KenKnight et al. |
| 7,047,065 B2 | 5/2006 | Kalgren et al. |
| 7,062,325 B1 | 6/2006 | Krig et al. |
| 7,065,397 B2 | 6/2006 | Galen et al. |
| 7,072,708 B1 | 7/2006 | Andersen et al. |
| 7,074,195 B2 | 7/2006 | Nelson et al. |
| 7,079,895 B2 | 7/2006 | Verbeek et al. |
| 7,110,804 B2 | 9/2006 | Baumer et al. |
| 7,110,817 B2 | 9/2006 | Yu et al. |
| 7,113,825 B2 | 9/2006 | Pastore et al. |
| 7,115,096 B2 | 10/2006 | Siejko et al. |
| 7,123,962 B2 | 10/2006 | Siejko et al. |
| 7,127,290 B2 | 10/2006 | Girouard et al. |
| 7,158,830 B2 | 1/2007 | Yu et al. |
| 7,209,786 B2 | 4/2007 | Brockway et al. |
| 7,215,992 B2 | 5/2007 | Stahmann et al. |
| 7,248,923 B2 | 7/2007 | Maile et al. |
| 7,260,429 B2 | 8/2007 | Siejko et al. |
| 7,662,104 B2 | 2/2010 | Siejko et al. |
| 2001/0007053 A1 | 7/2001 | Bardy |
| 2001/0012955 A1 | 8/2001 | Goedeke et al. |
| 2001/0039503 A1 | 11/2001 | Chan et al. |
| 2001/0047125 A1 | 11/2001 | Quy |
| 2002/0001390 A1 | 1/2002 | Kawaguchi |
| 2002/0002389 A1 | 1/2002 | Bradley et al. |
| 2002/0016548 A1 | 2/2002 | Stadler et al. |
| 2002/0016550 A1 | 2/2002 | Sweeney et al. |
| 2002/0019586 A1 | 2/2002 | Teller et al. |
| 2002/0026103 A1 | 2/2002 | Norris et al. |
| 2002/0026122 A1 | 2/2002 | Lee et al. |
| 2002/0026223 A1 | 2/2002 | Riff et al. |
| 2002/0035337 A1 | 3/2002 | Oka |
| 2002/0072684 A1 | 6/2002 | Stearns |
| 2002/0072777 A1 | 6/2002 | Lu |
| 2002/0082645 A1 | 6/2002 | Sweeney |
| 2002/0082660 A1 | 6/2002 | Stahmann et al. |
| 2002/0091415 A1 | 7/2002 | Lovett et al. |
| 2002/0107450 A1 | 8/2002 | Ogura |
| 2002/0123672 A1 | 9/2002 | Christphersom et al. |
| 2002/0128563 A1 | 9/2002 | Carlson et al. |
| 2002/0147401 A1 | 10/2002 | Oka |
| 2002/0151812 A1 | 10/2002 | Scheiner et al. |
| 2002/0151938 A1 | 10/2002 | Corbucci |
| 2002/0193670 A1 | 12/2002 | Garfield et al. |
| 2003/0004549 A1 | 1/2003 | Hill et al. |
| 2003/0009189 A1 | 1/2003 | Gilson et al. |
| 2003/0013974 A1 | 1/2003 | Natarajan et al. |
| 2003/0014083 A1 | 1/2003 | Kupper |
| 2003/0040676 A1 | 2/2003 | Prentice et al. |
| 2003/0045805 A1 | 3/2003 | Sheldon et al. |
| 2003/0045908 A1 | 3/2003 | Condie et al. |
| 2003/0055352 A1 | 3/2003 | Hayek et al. |
| 2003/0055461 A1 | 3/2003 | Girouard et al. |
| 2003/0060854 A1 | 3/2003 | Zhu |
| 2003/0069608 A1 | 4/2003 | Sweeney |

| | | |
|---|---|---|
| 2003/0072458 A1 | 4/2003 | Halleck et al. |
| 2003/0078624 A1 | 4/2003 | Carlson et al. |
| 2003/0093002 A1 | 5/2003 | Kuo |
| 2003/0093003 A1 | 5/2003 | Watrous et al. |
| 2003/0105496 A1 | 6/2003 | Yu et al. |
| 2003/0120159 A1 | 6/2003 | Mohler |
| 2003/0120313 A1 | 6/2003 | Begemann et al. |
| 2003/0120315 A1 | 6/2003 | Spinelli et al. |
| 2003/0125774 A1 | 7/2003 | Salo |
| 2003/0139778 A1 | 7/2003 | Fischell et al. |
| 2003/0144702 A1 | 7/2003 | Yu et al. |
| 2003/0144703 A1 | 7/2003 | Yu et al. |
| 2003/0158492 A1 | 8/2003 | Sheldon et al. |
| 2003/0158584 A1 | 8/2003 | Cates et al. |
| 2003/0171791 A1 | 9/2003 | KenKnight et al. |
| 2003/0176896 A1 | 9/2003 | Lincoln et al. |
| 2003/0191503 A1 | 10/2003 | Zhu et al. |
| 2003/0204206 A1 | 10/2003 | Padua et al. |
| 2003/0204231 A1 | 10/2003 | Hine et al. |
| 2003/0208240 A1 | 11/2003 | Pastore et al. |
| 2003/0216620 A1 | 11/2003 | Jain et al. |
| 2003/0229289 A1 | 12/2003 | Mohler et al. |
| 2003/0233130 A1 | 12/2003 | Padmanabhan et al. |
| 2003/0233132 A1 | 12/2003 | Pastore et al. |
| 2004/0024423 A1 | 2/2004 | Lincoln et al. |
| 2004/0038947 A1 | 2/2004 | Wink et al. |
| 2004/0039295 A1 | 2/2004 | Olbrich et al. |
| 2004/0039419 A1 | 2/2004 | Stickney et al. |
| 2004/0039420 A1 | 2/2004 | Jayne et al. |
| 2004/0064056 A1 | 4/2004 | Ogura |
| 2004/0073093 A1 | 4/2004 | Hatlestad |
| 2004/0078059 A1 | 4/2004 | Ding et al. |
| 2004/0078060 A1 | 4/2004 | Ding et al. |
| 2004/0102712 A1 | 5/2004 | Belalcazar et al. |
| 2004/0106960 A1 | 6/2004 | Siejko et al. |
| 2004/0106961 A1 | 6/2004 | Siejko et al. |
| 2004/0106962 A1 | 6/2004 | Mai et al. |
| 2004/0111040 A1 | 6/2004 | Ni et al. |
| 2004/0122484 A1 | 6/2004 | Hatlestad et al. |
| 2004/0127792 A1 | 7/2004 | Siejko et al. |
| 2004/0133247 A1 | 7/2004 | Stahmann et al. |
| 2004/0138572 A1 | 7/2004 | Thiagarajan |
| 2004/0167417 A1 | 8/2004 | Schulhauser et al. |
| 2004/0215264 A1 | 10/2004 | Van Bentem |
| 2004/0220637 A1* | 11/2004 | Zdeblick et al. ............... 607/17 |
| 2004/0225332 A1 | 11/2004 | Gebhardt et al. |
| 2004/0236239 A1 | 11/2004 | Murray et al. |
| 2004/0243192 A1* | 12/2004 | Hepp et al. ............... 607/17 |
| 2004/0254481 A1 | 12/2004 | Brodnick |
| 2004/0255956 A1 | 12/2004 | Vinten-Johansen et al. |
| 2004/0267147 A1 | 12/2004 | Sullivan |
| 2004/0267148 A1 | 12/2004 | Arand et al. |
| 2005/0004476 A1 | 1/2005 | Payvar et al. |
| 2005/0027323 A1 | 2/2005 | Mulligan et al. |
| 2005/0033190 A1 | 2/2005 | Bauer |
| 2005/0038345 A1 | 2/2005 | Gorgenberg et al. |
| 2005/0060001 A1 | 3/2005 | Singhal et al. |
| 2005/0065448 A1 | 3/2005 | Stahmann et al. |
| 2005/0075673 A1 | 4/2005 | Warkentin et al. |
| 2005/0090870 A1 | 4/2005 | Hine et al. |
| 2005/0102001 A1 | 5/2005 | Maile et al. |
| 2005/0102002 A1 | 5/2005 | Salo et al. |
| 2005/0137631 A1 | 6/2005 | Yu et al. |
| 2005/0148896 A1 | 7/2005 | Siejko et al. |
| 2005/0148897 A1 | 7/2005 | Cho et al. |
| 2005/0149136 A1 | 7/2005 | Siejko et al. |
| 2005/0197674 A1 | 9/2005 | McCabe et al. |
| 2005/0203579 A1 | 9/2005 | Sowelam et al. |
| 2005/0256542 A1 | 11/2005 | Pastore et al. |
| 2006/0015146 A1 | 1/2006 | Girouard et al. |
| 2006/0020294 A1 | 1/2006 | Brockway et al. |
| 2006/0020295 A1 | 1/2006 | Brockway et al. |
| 2006/0025699 A1 | 2/2006 | Maile et al. |
| 2006/0030892 A1 | 2/2006 | Kadhiresan et al. |
| 2006/0041280 A1 | 2/2006 | Stahmann et al. |
| 2006/0116593 A1 | 6/2006 | Zhang et al. |
| 2006/0149326 A1 | 7/2006 | Prinzen et al. |
| 2006/0161070 A1 | 7/2006 | Siejko et al. |
| 2006/0241704 A1 | 10/2006 | Shuros et al. |
| 2006/0253156 A1 | 11/2006 | Pastore et al. |
| 2006/0259087 A1 | 11/2006 | Baynham et al. |
| 2006/0259088 A1 | 11/2006 | Pastore et al. |
| 2006/0270939 A1 | 11/2006 | Wariar et al. |
| 2006/0282000 A1 | 12/2006 | Zhang et al. |
| 2006/0287684 A1 | 12/2006 | Baynham et al. |
| 2007/0021789 A1 | 1/2007 | Pastore et al. |
| 2007/0043393 A1 | 2/2007 | Brockway et al. |
| 2007/0054871 A1 | 3/2007 | Pastore et al. |
| 2007/0078491 A1 | 4/2007 | Siejko et al. |
| 2007/0150005 A1 | 6/2007 | Sih et al. |
| 2007/0162080 A1 | 7/2007 | Brockway et al. |
| 2007/0179392 A1 | 8/2007 | Zhang |
| 2008/0177191 A1 | 7/2008 | Patangay et al. |
| 2009/0287106 A1 | 11/2009 | Zhang et al. |
| 2010/0099997 A1 | 4/2010 | Siejko et al. |

FOREIGN PATENT DOCUMENTS

| | | |
|---|---|---|
| EP | 0474958 | 3/1992 |
| EP | 0522693 | 1/1993 |
| EP | 709058 A1 | 5/1996 |
| EP | 0762908 B1 | 3/1997 |
| EP | 1179317 A2 | 2/2002 |
| EP | 1247485 A1 | 10/2002 |
| JP | 2000-316825 | 11/2000 |
| WO | WO-9518649 A1 | 7/1995 |
| WO | WO-97/25098 | 7/1997 |
| WO | WO-99/10042 | 3/1999 |
| WO | WO-00/04947 | 2/2000 |
| WO | WO-00/09206 | 2/2000 |
| WO | WO-0041765 | 7/2000 |
| WO | WO-0041766 | 7/2000 |
| WO | WO-01/03575 | 1/2001 |
| WO | WO-01/08748 | 2/2001 |
| WO | WO-0115609 A1 | 3/2001 |
| WO | WO-0124876 A1 | 4/2001 |
| WO | WO-01/30436 | 5/2001 |
| WO | WO-0156651 A1 | 8/2001 |
| WO | WO-0167948 A2 | 9/2001 |
| WO | WO-01/76689 | 10/2001 |
| WO | WO-02/087694 | 11/2002 |
| WO | WO-03041797 A2 | 5/2003 |
| WO | WO-2004012815 A1 | 2/2004 |
| WO | WO-2004050178 A1 | 6/2004 |
| WO | WO-2004/060483 A1 | 7/2004 |
| WO | WO-2004058326 A2 | 7/2004 |
| WO | WO-2005122902 A1 | 12/2005 |
| WO | WO-2006028575 A2 | 3/2006 |
| WO | WO-2006028575 A3 | 3/2006 |
| WO | WO-2006074189 A1 | 7/2006 |
| WO | WO-2006078757 A1 | 7/2006 |
| WO | WO-2006115693 A2 | 11/2006 |
| WO | WO-2006115693 A3 | 11/2006 |
| WO | WO-2006124636 A2 | 11/2006 |
| WO | WO-2006124636 A3 | 11/2006 |
| WO | WO-2006124729 A2 | 11/2006 |
| WO | WO-2006124729 A3 | 11/2006 |
| WO | WO-2006127594 A2 | 11/2006 |
| WO | WO-2006127594 A3 | 11/2006 |

OTHER PUBLICATIONS

"U.S. Appl. No. 10/138,046 Non Final office action mailed Jun. 29, 2005", 14 pgs.

"U.S. Appl. No. 10/138,046 Notice of allowance mailed May 18, 2006", 6 pgs.

"U.S. Appl. No. 10/138,046 Notice of allowance mailed Nov. 29, 2005", 5 pgs.

"U.S. Appl. No. 10/138,046 Response filed Sep. 29, 2005 to Non Final office action mailed Jun. 29, 2005", 9 pgs.

"U.S. Appl. No. 10/307,896 Notice of allowance mailed May 30, 2006", 14 pgs.

"U.S. Appl. No. 10/307,896 Notice of allowance mailed Oct. 28, 2005", 14 pgs.

"U.S. Appl. No. 10/323,604 Final office action mailed Feb. 12, 2007", 13 pgs.

"U.S. Appl. No. 10/323,604 Non Final office action mailed Dec. 30, 2005", 27 pgs.

"U.S. Appl. No. 10/323,604 Response filed May 30, 2007 to Final office action mailed Feb. 12, 2007", 17 pgs.
"U.S. Appl. No. 10/323,604 Response filed Jun. 30, 2006 to Non Final office action mailed Dec. 30, 2005", 20 pgs.
"U.S. Appl. No. 10/323,604, Non-Final Office Action mailed Aug. 8, 2007", 15 pgs.
"U.S. Appl. No. 10/334,694 Non-Final Office Action Nov. 27, 2006", 14 pgs.
"U.S. Appl. No. 10/334,694 Non-Final Office Action Apr. 20, 2007", 28 pgs.
"U.S. Appl. No. 10/334,694 Response to Non-Final Office Action filed Feb. 27, 2007", 28 pgs.
"U.S. Appl. No. 10/334,694 Response to Non-Final Office Action filed Jul. 20, 2007", 18 Pages.
"U.S. Appl. No. 10/703,175, Final Office Action mailed Oct. 12, 2006", 10 pgs.
"U.S. Appl. No. 10/703,175, Non-Final Office Action mailed May 10, 2006", 13 pgs.
"U.S. Appl. No. 10/703,175, Notice of Allowance mailed Mar. 19, 2007", 6 pgs.
"U.S. Appl. No. 10/703,175, Response file Dec. 12, 2006 to Final Office Action mailed Oct. 12, 2006", 21 pgs.
" U.S. Appl. No. 10/703,175, Response filed Aug. 9, 2006 to Non-Final Office Action mailed May 10, 2006", 20 pgs.
"U.S. Appl. No. 10/746,874 Notice of Allowance mailed May 19, 2006", 13 pgs.
"U.S. Appl. No. 10/865,498 Non-Final Office Action mailed Sep. 11, 2006", 11 pgs.
"U.S. Appl. No. 10/865,498 Notice of Allowance mailed Dec. 6, 2006", 12 pgs.
"U.S. Appl. No. 10/865,498 Response to Non-Final Office Action filed Oct. 24, 2006", 23 pgs.
"U.S. Appl. No. 11/129,058 Final Office Action Received Jul. 9, 2007", 17 pgs.
"U.S. Appl. No. 11/129,058 Non Final office action mailed Jan. 29, 2007", 12 pgs.
"U.S. Appl. No. 11/129,058 Response filed Apr. 30, 2007 to Non Final office action mailed Jan. 29, 2007", 16 pgs.
"International Search Report and Written Opinion for Application No. PCT/US2006/001801, date mailed Jun. 16, 2006", 12 Pages.
"International Search Report and Written Opinion for Application No. PCT/US2006/018642, Date mailed Oct. 24, 2006", 14 Pages.
"Non-Final Office Action mailed by the USPTO on Mar. 31, 2006 for related matter U.S. Appl. No. 10/788,906", 41 Pages.
"Non-Final Office Action Response Filed Jun. 30, 2006 with the USPTO for related matter U.S. Appl. No. 10/788,906", 26 Pages.
"Restriction Requirement Mailed Aug. 1, 2007 in U.S. Appl. No. 11/129,050", RERR,6 pgs.
Aaron, S. D., et al., "How accurate is spirometry at predicting restrictive pulmonary impairment?", *Chest*, 115(3), (Mar. 1999),869-873.
Airaksinen, K. E., et al., "Antiarrhythmic effect of repeated coronary occlusion during balloon angioplasty", *J Am Coll Cardiol.*, 29(5), (Apr. 1997),1035-1038.
Amende, I. , "Hemodynamics in ischemia: diastolic phase", *Z. Kardiol., 73 Suppl 2*, [Article in German With English Abstract],(1984),127-33.
Arnaud, Claire , et al., "iNOS is a mediator of the heat stress-induced preconditioning against myocardial infarction in vivo in the rat", *Cardiovascular Research*, 58, (2003), 118-125.
Barbaro, V. , et al., "A portable unit for remote monitoring of pacemaker patients", *Journal of Telemedicine and Telecare*, 3(2), (1997),96-102.
Baynham, Tamara C., et al., "Integrated Catheter and Pulse Generator Systems and Methods", U.S. Appl. No. 11/468,875, filed Aug. 31, 2006, 23 Pages.
Bourge, Robert , et al., "Noninvasive Rejection Monitoring of Cardiac Transplants Using High Resolution Intramyocardial Electrograms", *PACE*, vol. 21, Part II, (Nov. 1998),2338-2344.
Braunwald, Nina S., et al., "Sustained Paired Electrical Stimuli; Slowing of the Ventricular Rate and Augmentation of Contractile Force", *American Journal of Cardiology*, 14, (1964),pp. 285 & 385-393.

Breithardt, O A., et al., "Acute effects of cardiac resynchronization therapy on functional mitral regurgitation in advanced systolic heart failure", *Journal of the American College of Cardiology*41(5), (May 21, 2003),765-70.
Brunner, Friedrich , "Attenuation of myocardial ischemia/reperfusion injury in mice with myocyte-specific overexpression of endothelial nitric oxide synthase", *Cardiovascular Research*, 57 , (2003),55-62.
Bulgrin, J. R., et al., "Comparison of Short-Time Fourier, Wavelet and Time-Domain Analyses of Intracardiac Sounds", *Biomedical Sciences Instrumentation*, 29, (1993),465-472.
Carabello, B A., "Mitral valve disease", *Current Problems in Cardiology*, 18(7), (Jul. 1993),423-78.
Carlson, Gerrard M., et al., "Hemodynamic Stability Assessment Based on Heart Sounds", U.S. Appl. No. 11/277,773, filed Mar. 29, 2006, 39 Pages.
Collins, Sean , "Diagnostic Utility of an S3 in Dyspneic ED Patients", *Inovise Medical Inc*, University of Cincinnati Medical Center, (2005),6 Pages.
Dzwonczyk, R. , et al., "Myocardial electrical impedance responds to ischemia and reperfusion in humans", *IEEE Transactions on Biomedical Engineering*51(12), (Dec. 2004),2206-2209.
ER, F. , et al., "Dominant-negative suppression of HCN channels markedly reduces the native pacemaker current I(f) and undermines spontaneous beating of neonatal cardiomyocytes.", *Circulation*, 107(3), Jan. 2003 ,485-9.
Fenster, M S., et al., "Mitral regurgitation: an overview", *Curr Probl Cardiol.*, 20(4), (Apr. 1995),193-280.
Ferdinandy, Peter , et al., "Nitric oxide, superoxide, and peroxynitrite in myocardial ischaemia-reperfusion injury and preconditioning", *British Journal of Pharmacology*, 138(4), (2003),532-543.
Flogel, Ulrich , "Myoglobin: A scanvenger of bioactive NO", *PNAS*, 98(2), (Jan. 16, 2001),735-740.
Gewaltig, Michael T., "Vasoprotection by nitric oxide: mechanisms and therapeutic potential", *Cardiovascular Research*, 55, (Feb. 14, 2002),250-260.
Hada, Yoshiyuki , et al., "Pulsus alternans determined by biventricular simultaneous systolic time intervals", *Circulation*, 65(3), (Mar. 1982),617-26.
Haro, Carlos , et al., "Respiration-Synchronized Heart Sound Trending", U.S. Appl. No. 11/561,428, filed Nov. 20, 2006, 54 Pages.
Henriques, Josep P., et al., "Outcome of primary angioplasty for acute myocardial infarction during routine duty hours versus during off-hours", *J Am Coll Cardiol*, 41(12), (Jun. 18, 2003),2138-2142.
Hutten, H. , et al., "Cardiac pacemaker as bridge to cardiac telemonitoring", *Biomedizinische Technik, 41(6), Institut für Elektro- und Biomedizinische Technik Technische Universitat Graz*, [Article in German With English Abstract], (Jun. 1996),158-165.
Hutten, H. , et al., "Cardiac Telemonitoring through the Linkage of Close-up Telemetry and Internet Transmission", *Institute for Electro- and Biomedical Technology, Technical University of Graz Inffeldgasse*, 42, [Article in German with English Abstract],(1997),67-69.
Ishihara, M. , et al., "Implications of prodromal angina pectoris in anterior wall acute myocardial infarction: acute angiographic findings and long-term prognosis", *J Am Coll Cardiol.*, 30(4), (1997),970-5.
Ji, J. , "An Ultraminiature CMOS Pressure Sensor for a Multiplexed Cardiovascular Catheter", *IEEE Transactions on Electron Devices*, vol. 39, No. 10, (Oct. 1992),pp. 2260-2267.
Kameli, Nader , "Integrated System for Managing Patients With Heart Failure", U.S. Appl. No. 11/553,103, filed Oct. 26, 2006, 41 Pages.
Kin, Hajime , et al., "Postconditioning attenuates myocardial ischemia-reperfusion injury by inhibiting events in the early minutes of reperfusion", *Cardiovascular Research*, 62(1), (Apr. 1, 2004), 74-85.
Kinderman, Michael , et al., "Optimizing the AV Delay in DDD Pacemaker Patients with High Degree AV Block: Mitral Valve Doppler Versus Impedance Cardiography", *Pace*, vol. 20, (Oct. 1997),2453-2462.

Kis, A., "Repeated cardiac pacing extends the time during which canine hearts are protected against ischaemia-induced arrhythmias : role of nitric oxide.", *Journal of Molecular and Cellular Cardiology*, 31(6), (Jun. 1999),1229-1241.

Kloner, R. A., et al., "Prospective temporal analysis of the onset of preinfarction angina versus outcome: an ancillary study in TIMI-9B", *Circulation*, 97(11), (1998),1042-5.

Koning, M M., "Rapid ventricular pacing produces myocardial protection by nonischemic activation of KATP+ channels", *Circulation*, 93(1), (Jan. 1, 1996), 178-186.

Konta, Tsuyoshi , et al., "Significance of Discordant ST Alternans in Ventricular Fibrillation", *Circulation*, 82(6), (Dec. 1990),2185-2189.

Krayenbuhl, H. P., "Hemodynamics in ischemia. Systolic phase", *Z. Kardiol.*, 73 Suppl 2, [Article in German with English Abstract], (1984),119-25.

Leatham, A , "Splitting of the First and Second Heart Sounds", *Lancet*, 267 (6839), (Sep. 25, 1954),607-614.

Lee, Y. C., et al., "Pulsus alternans in patients with congestive cardiomyopathy", *Circulation*, 65(7), (Jun. 1982),1533-4.

Leonelli, Fabio M., et al., "Systolic and Diastolic Effects of Variable Atroventricular Delay and Patients with Complete Hear Block and Normal Ventricular Function", *Amer. J-Cardiology*, vol. 80, (Aug. 1, 1997),294-298.

Li, Qianghong , "Gene Therapy With Inducible Nitric Oxide Synthase Protects Against Myocardial Infarction via a Cyclooxygenase-2-Dependent Mechanism", *Circulation Research*, 92, (2003),741-748.

Loukogeorgakis, S. P., et al., "Remote ischemic preconditioning provides early and late protection against endothelial ischemia-reperfusion injury in humans: role of the autonomic nervous system.", *J Am Coll Cardiol.*, 46(3), (Aug. 2, 2005),450-6.

Makhoul, John , "Linear Prediction: A Tutorial Review", *Proceedings of the IEEE*, 63, (Apr. 1975),561-580.

Marcus, G. M., et al., "Association Between Phonocardiographic Third and Fourth Heart Sounds and Objective Measures of Left Ventricular Function", *JAMA*, 293(18), (May 11, 2005),2238-44.

Meier, B. , et al., "Coronary Pacing During Percutaneous Transluminal Coronary Angioplasty", *Therapy And Prevention Cardiac Pacing*, 71(3), (Mar. 1985),557-561.

Melo, L. G., et al., "Molecular and cell-based therapies for protection, rescue, and repair of ischemic myocardium: reasons for cautious optimism,", *Circulation*, 109(20), (May 2004),2386-93.

Mower, Morton , U.S. Patent Office Patent Application Information Retrieval search results for U.S. Appl. No. 10/214,474, filed Aug. 8, 2002, entitled *"Method and Apparatus for Treating Hemodynamic Disfunction"*, 3.

Murry, C. E., "Preconditioning with ischemia: a delay of lethal cell injury in ischemic myocardium", *Circulation*, 74(5), (1986),1124-1136.

Obaidat, M. S., et al., "Performance of the Short-Time Fourier Transform and Wavelet Transform to Phonocardiogram Signal Analysis", *Proceedings of the 1992 ACM/SIGAPP Symposium on Applied Computing ACM*, Applied Computing: Technological Challenges of the 1990s,(1992),856-862.

Obaidat, M. S., et al., "Performance of the short-time Fourier transform and wavelet transform to phonocardiogram signal analysis", *Database Inspec* [Online] *The Institution of Electrical Engineers*, Stevenage, GB, (1992).

Ostadal, Petr , et al., "The effect of early treatment by cerivastatin on the serum level of C-reactive protein, interleukin-6, and interleukin-8 in patients with unstable angina and non-Q-wave myocardial infarction", *Molecular and Cellular Biochemistry* 246, (2003),45-50.

Ovize, M. , et al., "Stretch preconditions canine myocardium.", *Am J Physiol.*, 266(1 Pt 2), (Jan. 1994),H137-46.

Palomo, A R., et al., "Echo-phonocardiographics determination of left atrial and left ventrical filling pressures with and without mitral stenosis", *Circulation*, vol. 61, No. 5, (May 1980),1043-1047.

Panju, Akbar A., et al., "Is This Patient Having a Myocardial Infarction?", *JAMA*, 280(14), (Oct. 14, 1998),1256-1263.

Paolocci, Nazareno , et al., "Positive inotropic and lusitropic effects of HNO/NO—in failing hearts: Independence from beta-adrenergic signaling", *Proceedings of the National Academy of Sciences USA*, 100(9), (Apr. 29, 2003),5537-5542.

Patangay , Ahilash , et al., "Ischemia Detection Using Heart Sound Timing", U.S. Appl. No. 11/625,003, filed Jan. 19, 2007, 69 Pages.

Pinchak, Alfred C., et al., "Multiaxial Accelerometers", *Encyclopedia of Medical Devices and Instrumentation, vol. 1, Department of Electrical and Computer Engineering*(1988),11 Pages.

Prinzen, Frits W., "Mapping of regional myocardial strain and work during ventricular pacing: experimental study using magnetic resonance imaging tagging", *Journal of the American College of Cardiology*, 33(6), (May 1999),1735-1742.

Qu, J , et al., "HCN2 overexpression in newborn and adult ventricular myocytes: distinct effects on gating and excitability", *Circ. Res.*, vol. 89(1), (Jul. 6, 2001),e8-14.

Ritter, P. , et al., "A Built-In System Based on the Peak Endocardial Acceleration (PEA) for AV-Delay Optimation in DDDR Pacing", *PACE*, 20(5) (Part II), (Abstract of Paper presented at EUROPACE '97), (May 1997),1567.

Ritter, P. , et al., "New Method for Determining the Optimal Atrio-Ventricular Delay in Patients Place in DDD Mode for Complete Atrio-Ventricular Block", *NASPE abstract #237*, (1995),885.

Rubenstein, Donald S., et al., "Premature Beats Elicit a Phase Reversal of Mechanoelectrical Alternans in Cat Ventricular Myocytes", *Circulation*, vol. 91, No. 1, American Heart Association,(Jan. 1, 1995),201-214.

Sabbah, Hani N., et al., "Delivery of Non-Excitatory Contractility-Modulation Electric Signals Improve Left Ventricular Performance in Dogs with Heart Failure", *Circulation, Supplement 1*, 100 (18), Abstract No. 631,(Nov. 2, 1999),pp. 1-122.

Salerno, D. M., "Seismocardiography for monitoring changes in left ventricular function during ischemia.", *Chest*, 100(4), (Oct. 1991),991-3.

Salloum, Fadi , "Sildenafil Induces Delayed Preconditioning Through Inducible Nitric Oxide Synthase-Dependent Pathway in Mouse Heart", *Circulation Research*, 92, (Apr. 4, 2003),595-597.

Say, O , et al., "Classification of heart sounds by using wavelet transform", *24th Annual Conference and the Annual Fall Meeting of the Biomedical Engineering Society] EMBS/BMES Conference* vol. 1, (2002),128-129.

Schaefer, Saul , et al., "Clinical and hemodynamic characteristics of patients with inducible pulsus alternans", *American Heart Journal*, vol. 115, No. 6, (Jun. 1988),1251-7.

Schoemaker, R. G., et al., "Bradykinin mediates cardiac preconditioning at a distance", *Am J Physiol Heart Circ Physiol.*, 278(5), (May 2000),H1571-6.

Smith, R.A. , et al., "An intranet database for pacemaker patients", *International Journal of Medical Informatics*, 47, (1997),79-82.

Smith, Damon , et al., "Influence of the Aortic Component of the Second Heart Sound on Left Ventricular Maximal Negative dP/dt in the Dog", *Am. J. Cardiol.*, 55: 205, (1985),205-209.

Solomon, S. D., et al., "Angina pectoris prior to myocardial infarction protects against subsequent left ventricular remodeling", *J Am Coll Cardiol.*, 43(9), 2004,1511-4.

Stein, Emanuel , et al., "Rapid Interpretation of Heart Sounds and Murmurs", *Baltimore : Williams & Wilkins*, 4th ed.,1997 ,85-105.

Suematsu, Yoshihiro , et al., "L-Arginine given after ischaemic preconditioning can enhance cardioprotection in isolated rat hearts", *European Journal of Cardio-thoracic Surgery*, 19, (2001),873-879.

Tavel, Morton E., "The Appearance of Gallop Rhythm after Exercise Stress Testing", *Clin. Cardiol.*, vol. 19, (1996),887-891.

Tsang, A. , et al., "Postconditioning: a form of "modified reperfusion" protects the myocardium by activating the phosphatidylinositol 3-kinase-Akt pathway", *Circ Res.*, 95(3), Epub Jul. 8, 2004,(Aug. 6, 2004),230-2.

Vanagt, Ward Y., et al., "Ventricular Pacing for Improving Myocardial Tolerance to Ischemia, Progress Report on Project Guidant-CARIM", (Oct. 2003).

Vegh, A , et al., "Transient ischaemia induced by rapid cardiac pacing results in myocardial preconditioning", *Cardiovascular Research*, 25(12), (Dec. 1991), 1051-3.

Wariar, Ramesh , et al., "Detection of Myocardial Ischemia From the Time Sequence of Implanted Sensor Measurements", U.S. Appl. No. 11/426,835, filed Jun. 27, 2006, 41 Pages.

Watanabe, Michiko, et al., "Developmental Remodeling and Shortening of Cardiac Outflow Tract Involves Myocyte Programmed Cell Death", *Development*, 125 (19), (1998),3809-3820.

Woldbaek, Per R., et al., "Increased cardiac IL-18 mRNA, pro-IL-18 and plasma IL-18 after myocardial infarction in the mouse; a potential role in cardiac dysfunction", *Cardiovascular Research*, 59, (2003),122-131.

Wolfrum, Sebastian, et al., "Acute Reduction of Myocardial Infarct Size By a Hydroxymethyl Glutaryl Coenzyme A Reductase Inhibitor Is Mediated By Endothelial Nitric Oxide Synthase", *J. Cardiovas Pharmacol*, vol. 41, No. 3, (Mar. 2003),474-480.

Wood, J. C., et al., "Time-Frequency Transforms: A New Approach to First Heart Sound Frequency Dynamics", *IEEE Transactions on Biomedical Engineering*, 39 (7), IEEE Service Center, US,(Jul. 1, 1992),730-740.

Wu, Zhong-Kai, et al., "Ischemic preconditioning suppresses ventricular tachyarrhythmias after myocardial revascularization", *Circulation*, 106(24), (Dec. 10, 2002),3091-3096.

Wunderlich, Carsten, "Acute Inhibition of Myoglobin Impairs Contractility and Energy State of iNOS-Overexpressing Hearts", *Circulation Research*, 92, (2003),1352-1358.

Yang, S. M., et al., "Multiple, brief coronary occlusions during early reperfusion protect rabbit hearts by targeting cell signaling pathways", *Journal of the American College of Cardiology* 44(5), (Sep. 1, 2004),1103-1110.

Zanon, F, et al., "Reduced mitral regurgitation in heart failure patients submitted to cardiac resynchronization therapy: a short-term prospective study", *Italian Heart Journal*, 5(11), (Nov. 2004),826-30.

Zhao, Zhi-Qing, et al., "Inhibition of myocardial injury by ischemic postconditioning during reperfusion: comparison with ischemic preconditioning", *Am J Physiol Heart Circ Physiol*, 285(2), (Aug. 2003),H579-H588.

Zin, Z M., et al., "Wavelet analysis and classification of Mitral regurgitation and normal heart sounds based on artificial neural networks", *Seventh International Symposium on Signal Processing and Its Applications*, vol. 2, (Jul. 1-4, 2003),619-620.

"U.S. Appl. No. 10/334,694 Notice of Allowance mailed Oct. 5, 2010", 6 pgs.

* cited by examiner

SYSTEMS AND METHODS FOR VALVULAR REGURGITATION DETECTION

CROSS-REFERENCE TO RELATED APPLICATIONS

This application is related to the following, commonly assigned U.S. Patent Applications: Ser. No. 10/900,570 entitled "DETERMINING A PATIENT'S POSTURE FROM MECHANICAL VIBRATIONS OF THE HEART," filed on Jul. 28, 2004, now issued as U.S. Pat. No. 7,559,901; Ser. No. 10/703,175, entitled "A DUAL USE SENSOR FOR RATE RESPONSIVE PACING AND HEART SOUND MONITORING," filed on Nov. 6, 2003, now issued as U.S. Pat. No. 7,248,923; Ser. No. 10/334,694 entitled "METHOD AND APPARATUS FOR MONITORING OF DIASTOLIC HEMODYNAMICS," filed on Dec. 30, 2002, Ser. No. 10/746,874 entitled "A THIRD HEART SOUND ACTIVITY INDEX FOR HEART FAILURE MONITORING," filed on Dec. 24, 2003, now issued as U.S. Pat. No. 7,115,096; Ser. No. 11/037,275, entitled "METHOD FOR CORRECTION OF POSTURE DEPENDENCE ON HEART SOUNDS," filed on Jan. 18, 2005, now issued as U.S. Pat. No. 7,662,104; Ser. No. 60/631,742 entitled "CARDIAC ACTIVATION SEQUENCE MONITORING FOR ISCHEMIA DETECTION," filed on Nov. 30, 2004, Ser. No. 11/129,050, entitled "METHOD AND APPARATUS FOR CARDIAC PROTECTION PACING," filed on May 16, 2005, and Ser. No. 11/148,107, entitled "ISCHEMIA DETECTION USING HEART SOUND SENSOR," filed on Jun. 8, 2005, each of which is hereby incorporated by reference.

TECHNICAL FIELD

The field generally relates to implantable medical devices and, in particular, but not by way of limitation, to systems and methods for monitoring mechanical activity of the heart.

BACKGROUND

Implantable medical devices (IMDs) are devices designed to be implanted into a patient. Some examples of these devices include cardiac function management (CFM) devices such as implantable pacemakers, implantable cardioverter defibrillators (ICDs), cardiac resynchronization devices, and devices that include a combination of such capabilities. The devices are typically used to treat patients using electrical or other therapy and to aid a physician or caregiver in patient diagnosis through internal monitoring of a patient's condition. The devices may include one or more electrodes in communication with sense amplifiers to monitor electrical heart activity within a patient, and often include one or more sensors to monitor one or more other internal patient parameters. Other examples of implantable medical devices include implantable diagnostic devices, implantable insulin pumps, devices implanted to administer drugs to a patient, or implantable devices with neural stimulation capability.

Blood flows from the left atrium to the left ventricle through the mitral valve during diastole or the filling phase. During systole, the mitral valve is closed and blood is ejected through the aortic valve by the contraction of the left ventricle. A defective or partially closed mitral valve can cause blood to leak and cause turbulence near the mitral annulus. This leakage is called mitral regurgitation (MR). MR can also occur with a normal mitral valve due to a dilated and dyssynchronous left ventricle, which may be caused by cardiovascular disease. Improper atrial-ventricular delay (AV delay) can cause left ventricular dyssynchrony, which can lead to a partially closed mitral valve, in turn causing MR. MR also refers to regurgitation due to mitral stenosis, and mitral valve prolapse.

Blood flows from the right atrium to the right ventricle through the tricuspid valve during diastole. During systole, the tricuspid valve is closed and blood is ejected through the pulmonic valve by the contraction of the right ventricle. A defective or partially closed tricuspid valve can cause blood to leak backward through the tricuspid valve. This leakage is called tricuspid regurgitation (TR). Typically, TR occurs due to a defective tricuspid valve, but can also occur due to cardiac disease. Other forms of regurgitation include aortic regurgitation (AR), which includes regurgitation due to aortic stenosis. Valvular regurgitation (VR) refers to MR, or TR, or AR, or any combination of two or more of MR, TR, and AR. VR can make it difficult for the heart to increase blood flow during times of higher demand, such as during exercise.

It is believed that MR increases with congestive heart failure decompensation. It is also believed that ten percent of MR is caused by ischemia. A mitral valve or tricuspid valve of a heart can become damaged through infection or disease. Certain diet medications have been known to cause valvular damage. Acute MR resulting from myocardial infarction may have sixty to eighty percent mortality if it is present with severe pulmonary edema. Chronic MR may lead to severe left ventricle dysfunction, chronic congestive heart failure, or atrial fibrillation. The present inventors have recognized a need for improved sensing of events related to cardiac activity.

SUMMARY

This document discusses, among other things, systems and methods for monitoring mechanical activity of the heart. A system embodiment includes an implantable medical device (IMD). The IMD includes an implantable sensor operable to produce an electrical signal representative of mechanical activity of a heart of a subject and a controller circuit coupled to the sensor. The controller circuit includes a wavelet filter module and a valvular regurgitation (VR) calculation module. The wavelet filter module is configured to extract signal energy information related to VR from the electrical signal. The energy information includes variation of signal amplitude with frequency and time. The VR calculation module is configured to calculate a measurement of VR for one or more heartbeats using the energy information.

A method embodiment includes sensing an electrical signal representative of mechanical activity of a heart of a subject, extracting energy information from the electrical signal using wavelet filtering, and calculating a measurement of VR for one or more heartbeats using the energy information. The energy information includes a variation of signal amplitude with frequency and time. The VR measurement includes a ratio of energy of the electrical signal representative of VR during systole to energy of the electrical signal during diastole.

This summary is intended to provide an overview of the subject matter of the present patent application. It is not intended to provide an exclusive or exhaustive explanation of the invention. The detailed description is included to provide further information about the subject matter of the present patent application.

DETAILED DESCRIPTION

In the following detailed description, reference is made to the accompanying drawings which form a part hereof, and specific embodiments in which the invention may be practiced are shown by way of illustration. It is to be understood that other embodiments may be used and structural or logical changes may be made without departing from the scope of the present invention.

Valvular regurgitation (VR) is manifested as a turbulent blood flow in the left or right atrium or near the aortic valve during systole. VR refers to mitral regurgitation (MR), or tricuspid regurgitation (TR), or aortic regurgitation (AR), or a combination of two or more of MR, TR, and AR. Some amount of VR is believed present during early systole in eighty percent of patients exhibiting interventricular dyssynchrony between their right and left ventricles. Sensors can be included in implantable medical devices (IMDs) to provide internal patient diagnosis. The output from one or more sensors appropriate to sense mechanical heart activity (in contrast to electrical activity) can be used to provide a measure of VR. Examples of such sensors include those used to detect pressure changes in the heart due to VR or to detect mechanical vibrations of the heart that indicate VR. If the VR is a result of dyssynchrony of the left ventricle, a CFM device can restore proper synchrony, such as by providing or adjusting a proper atrial-ventricular (AV) delay, left ventricular pacing, or biventricular pacing.

Figure 1:
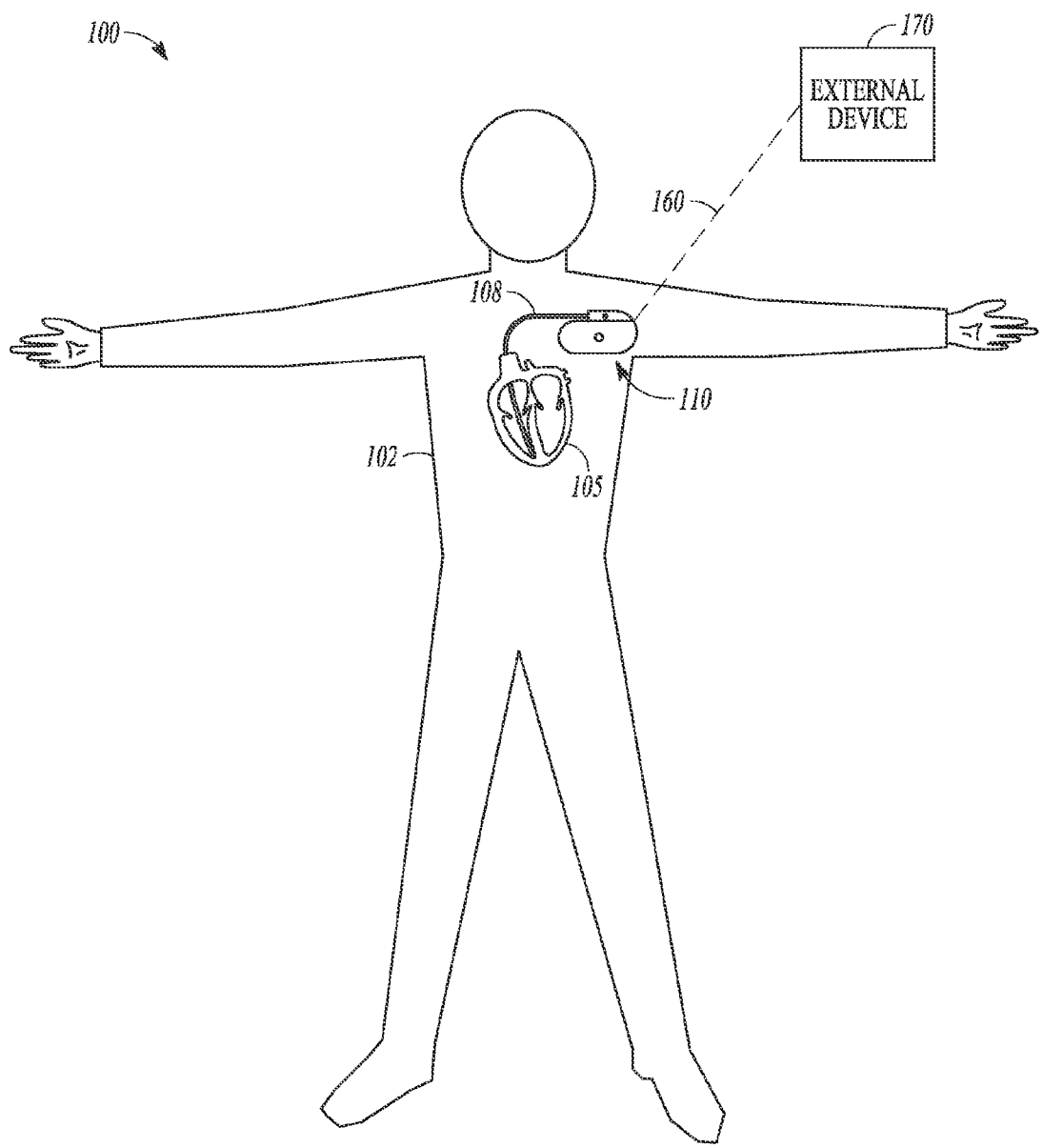
FIG. 1 is a block diagram of portions of a system that uses an implantable medical device.

FIG. 1 is a block diagram of portions of a system 100 that uses an implantable medical device (IMD) 110. As one example, the system 100 shown is used to treat a cardiac arrhythmia. The IMD 110 includes an electronics unit coupled by a cardiac lead 108, or additional leads, to a heart 105 of a patient 102, or otherwise associated with the heart 105. Examples of IMD 110 include, without limitation, a pacer, a defibrillator, a cardiac resynchronization therapy (CRT) device, or a combination of such devices. System 100 also typically includes an IMD programmer or other external device 170 that communicates wireless signals 160 with the IMD 110, such as by using radio frequency (RF) or other telemetry signals.

Cardiac lead 108 includes a proximal end that is coupled to IMD 110 and a distal end, coupled by an electrode or electrodes to one or more portions of a heart 105. The electrodes typically deliver cardioversion, defibrillation, pacing, or resynchronization therapy, or combinations thereof to at least one chamber of the heart 105. The electronics unit of the IMD 110 typically includes components that are enclosed in a hermetically-sealed canister or "can." Other electrodes may be located on the can, or on an insulating header extending from the can, or on other portions of IMD 110, such as for providing pacing energy, defibrillation energy, or both, in conjunction with the electrodes disposed on or around a heart 105. The lead 108 or leads and electrodes may also typically be used for sensing intrinsic or other electrical activity of the heart 105.

Figure 2:
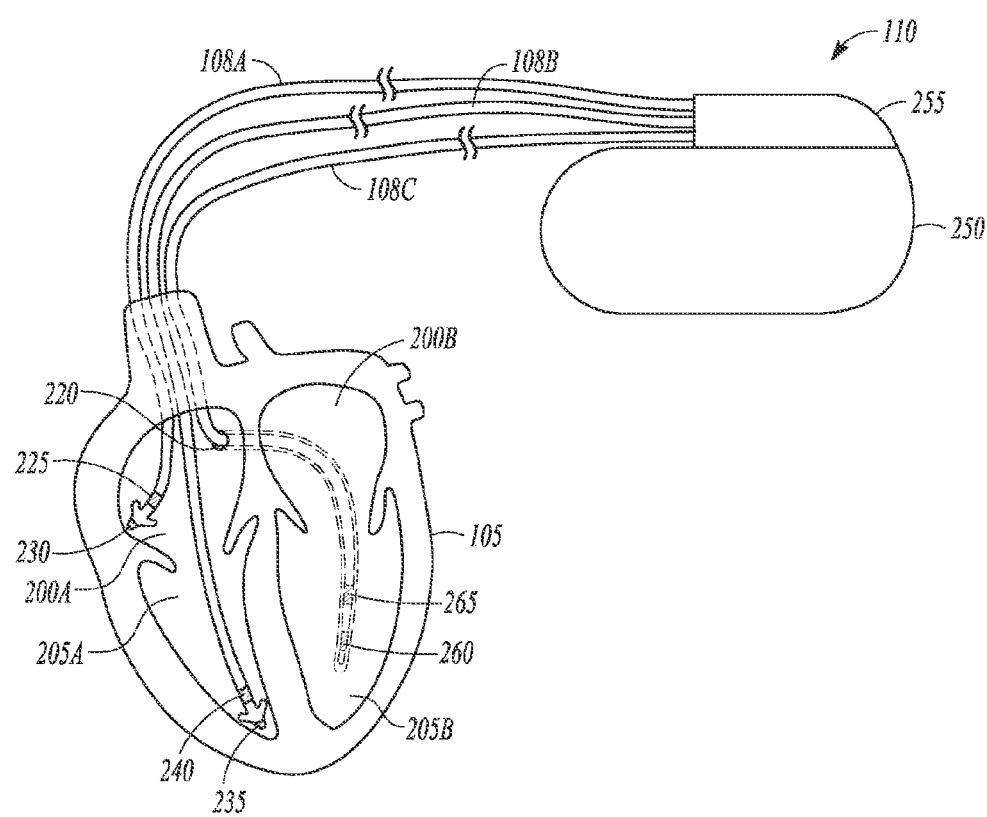
FIG. 2 illustrates an implantable medical device coupled by one or more leads to a heart.

FIG. 2 illustrates an IMD 110 coupled by one or more leads 108A-C to heart 105. Heart 105 includes a right atrium 200A, a left atrium 200B, a right ventricle 205A, a left ventricle 205B, and a coronary sinus 220 extending from right atrium 200A. Atrial lead 108A includes electrodes (electrical contacts, such as ring electrode 225 and tip electrode 230) disposed in an atrium 200A of heart 105 for sensing signals, or delivering pacing therapy, or both, to the atrium 200A. Ventricular lead 108B includes one or more electrodes, such as tip electrode 235 and ring electrode 240, for sensing signals, delivering pacing therapy, or both sensing signals and delivering pacing therapy. Sensing and pacing allows the IMD 110 to adjust timing of the chamber contractions. For example, IMD 110 can adjust the timing of ventricular contractions with respect to the timing of atrial contractions delay by sensing a contraction in the right atrium 200A and pacing the right ventricle 205A at the desired AV delay time.

Lead 108B optionally also includes additional electrodes, such as for delivering atrial cardioversion, atrial defibrillation, ventricular cardioversion, ventricular defibrillation, or combinations thereof to heart 105. Such electrodes typically have larger surface areas than pacing electrodes in order to handle the larger energies involved in defibrillation. Optionally, leads 108A and 108B are combined into one lead containing four electrodes located sequentially along the lead. In an example, a first tip electrode is located in the apex of the right ventricle 205A, a first ring electrode located proximal to the tip electrode and in the right ventricle 205A, a second ring electrode located proximal to the first ring electrode and in the right atrium 200A, and a third ring electrode located proximal to the second ring electrode and also located in the right atrium 200A.

In certain examples, a third cardiac lead 108C is attached to the IMD 110 through the header 255. The third lead 108C typically includes ring electrodes 260 and 265 placed in a coronary vein 220 extending along a wall of the left ventricle (LV) 205B. Lead 108B and 108C optionally provide resynchronization therapy to the heart 105.

Figure 3A:
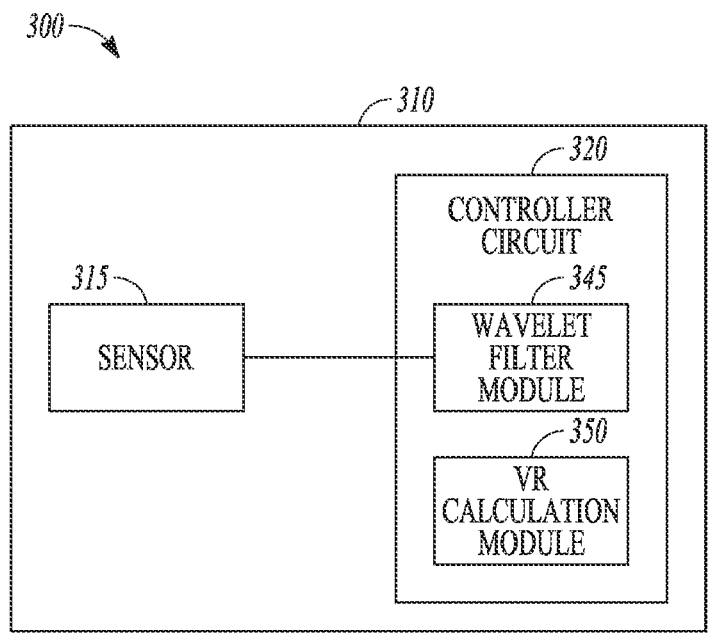
FIGS. 3A and 3B show embodiments of portions of systems that detect VR using implantable medical devices.
Figure 3B:
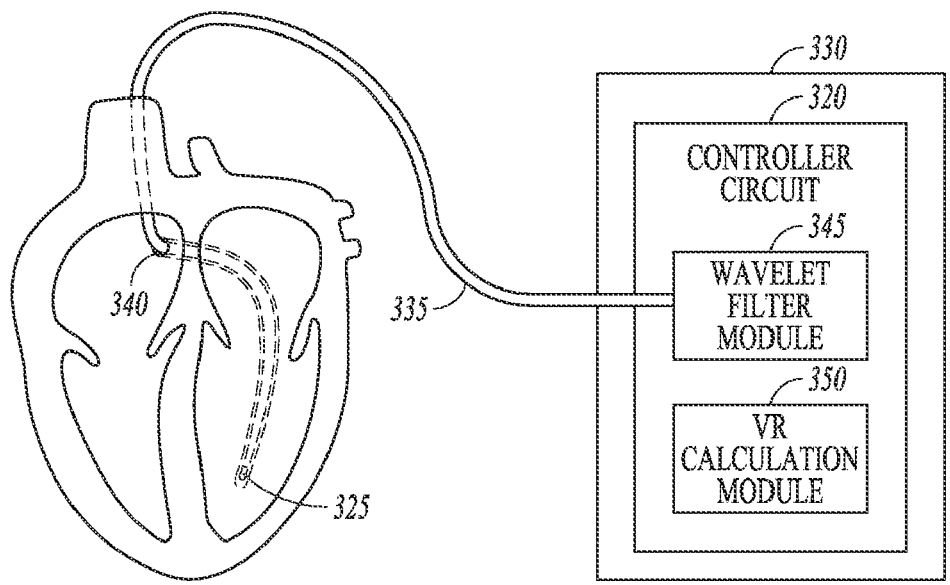

FIGS. 3A-B show embodiments of portions of systems 300 that detect VR using IMDs. In the embodiment of FIG. 3A, the IMD 310 includes an implantable sensor 315 coupled to a controller circuit 320. The implantable sensor 315 produces an electrical signal representative of mechanical activity of a heart. In FIG. 3A the sensor 315 is located within the can of the IMD 310. Examples of sensors that produce an electrical signal representative of mechanical activity of the heart of a subject from within an IMD include an accelerometer and a microphone. FIG. 3B shows a sensor 325 that is placed outside of the can of an IMD 330. In this example, the sensor 325 includes its own hermetically sealed housing and is coupled to the controller circuit 320, such as by an electrical lead 335. Examples of a sensor 325 that produces an electrical signal representative of mechanical activity of the heart which is placed outside of the IMD can include a pressure sensor, microphone, and an accelerometer. The example of the sensor 325 shown represents a pressure sensor on the tip of the electrical lead 335 placed in the coronary sinus 340. Descriptions of methods and systems for measuring left ventricular pressure are found in U.S. Pat. No. 6,666,826, Salo et al., entitled, "Method and Apparatus for Measuring Left Ventricular Pressure," which is hereby incorporated by reference. In other examples, a pressure sensor is placed in the right ventricle, right atrium, or the pulmonary artery.

The controller circuit 320 includes a wavelet filter module 345 and an VR calculation module 350. The wavelet filter module 345 extracts signal energy information from the electrical signal output by the implantable sensor 315 or 325. Wavelet analysis decomposes an electrical signal with both frequency and time. Therefore, the signal energy information includes variations of the amplitude of the electrical signal with both frequency and time.

Wavelet analysis overcomes a fundamental shortcoming of Fourier analysis. When an electrical signal is analyzed over a finite length of time, two problems can result. The first problem is time localization. Because the shape of the electrical signal waveform is highly dependent on the window of time used to sample the electrical signal, a window that is too long in time can cause localized time information in the electrical signal to be overlooked due to too much data or due to undersampling of the signal. The second problem is frequency localization. If the window is too short there may be too few oscillations to determine localized frequency information in the electrical signal. Fourier analysis can be viewed as representing a signal as a sum of sinusoidal waves. These sinusoids are well localized in frequency, but not in time. Thus, Fourier analysis can only show the frequency (spectral) information of the time signal analyzed.

One possibility for Fourier analysis would be to implement a windowed (or running) Fourier transform (short-time Fourier transform, or STFT). STFT uses a certain window size and slides it along the signal in time, computing the FFT at each time using only the data within the window, thereby producing a series of FFT transforms. However, the results are still dependent on the window size used. The main problem with the STFT is the inconsistent treatment of different frequencies; at low frequencies there so few oscillations within the window that it is not possible to extract localized frequency information, while at high frequencies there are so many oscillations that localized time information is lost. Additionally, the STFT still relies on the assumption that the signal can be decomposed into sinusoidal components.

In wavelet analysis, a scalable modulated window is typically shifted along the time domain electrical signal and for every position the frequency spectrum is calculated. This process is typically repeated many times with a slightly shorter (or longer) window for every new cycle of the electrical signal. By using a variable width window, wavelet analysis effectively zooms in on the signal when analyzing higher frequencies, thus providing higher resolution when necessary. The result is a collection of time-frequency representations of the signal having different resolutions.

Figure 4:
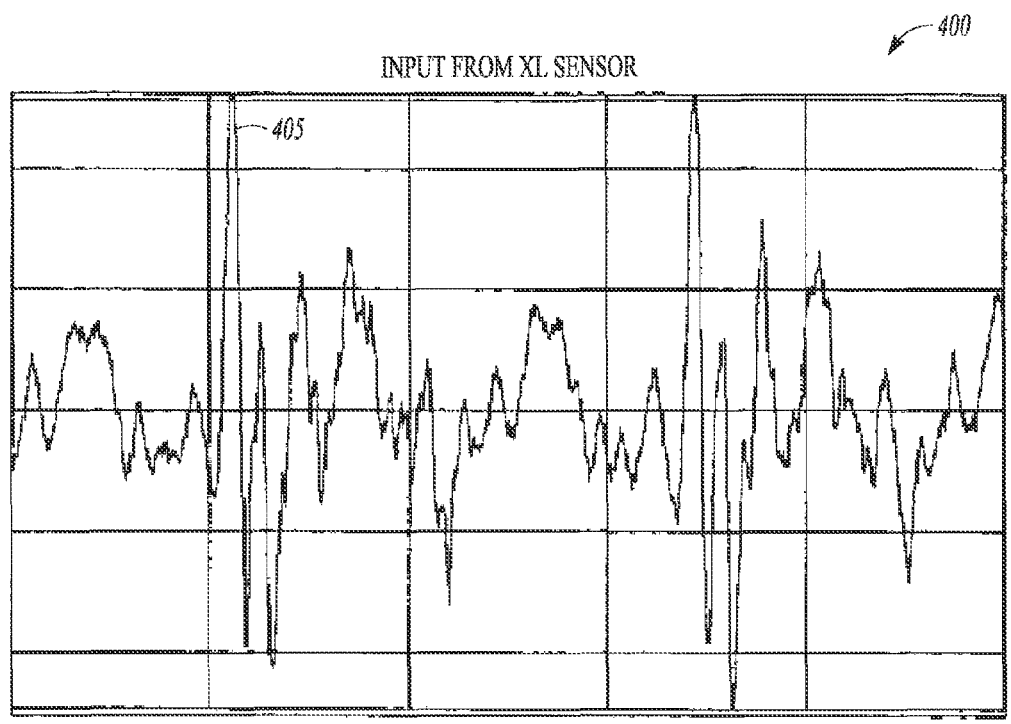
FIG. 4 shows a representation of a waveform of an electrical signal provided by a sensor.

FIG. 4 shows a representation of a waveform 400 of an electrical signal provided by a sensor to the wavelet filter 345. Because the sensor in this case was an accelerometer, the waveform 400 is an electrical signal that represents vibrations, including vibrations from the occurrence of VR. In certain examples, the bandwidth of the accelerometer is 0-500 hertz (Hz), i.e., at 500 Hz, the response of the accelerometer is twenty decibels (db) down from its highest response. In an example, an electrical signal output from an accelerometer is obtained by sampling the sensor output at 1000 Hz with twelve-bit quantization.

Figure 5:
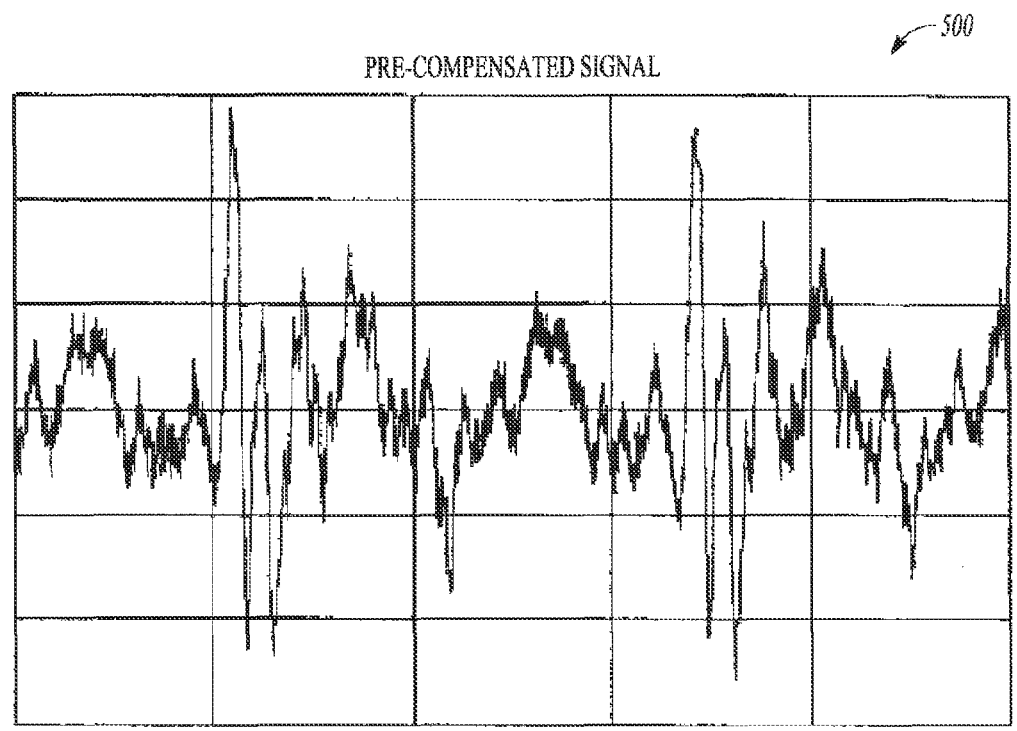
FIG. 5 shows a representation of a waveform of an electrical signal provided by a sensor that has been pre-compensated.

Some sensors have a low frequency response, i.e., the response of the sensors rolls off or is attenuated with higher frequencies. Such roll-off may be due to a transfer function of the sensor itself or from the interface between the sensor and human tissue. Electrical signals of interest in detecting VR may have frequency components where the sensor response is attenuated, such as from 100-500 Hz for example. For this reason, some embodiments include a pre-compensation circuit to compensate for such roll-off before the signal is processed by the wavelet filter module 345 of FIGS. 3A-B. The pre-compensation circuit is coupled between the sensor 315 or 325 and the controller circuit 320. An example of a pre-compensation circuit is an inverse filter circuit having high frequency gain, such as a high pass circuit having a response matched to a low pass response of a sensor or a sensor/tissue interface. Another example is a digital signal processor that adds high frequency gain to an electrical signal. FIG. 5 shows a waveform 500 that is a representation of the waveform in FIG. 4 after pre-compensation. Note that the signal 500 contains high frequency noise terms.

Figure 6:
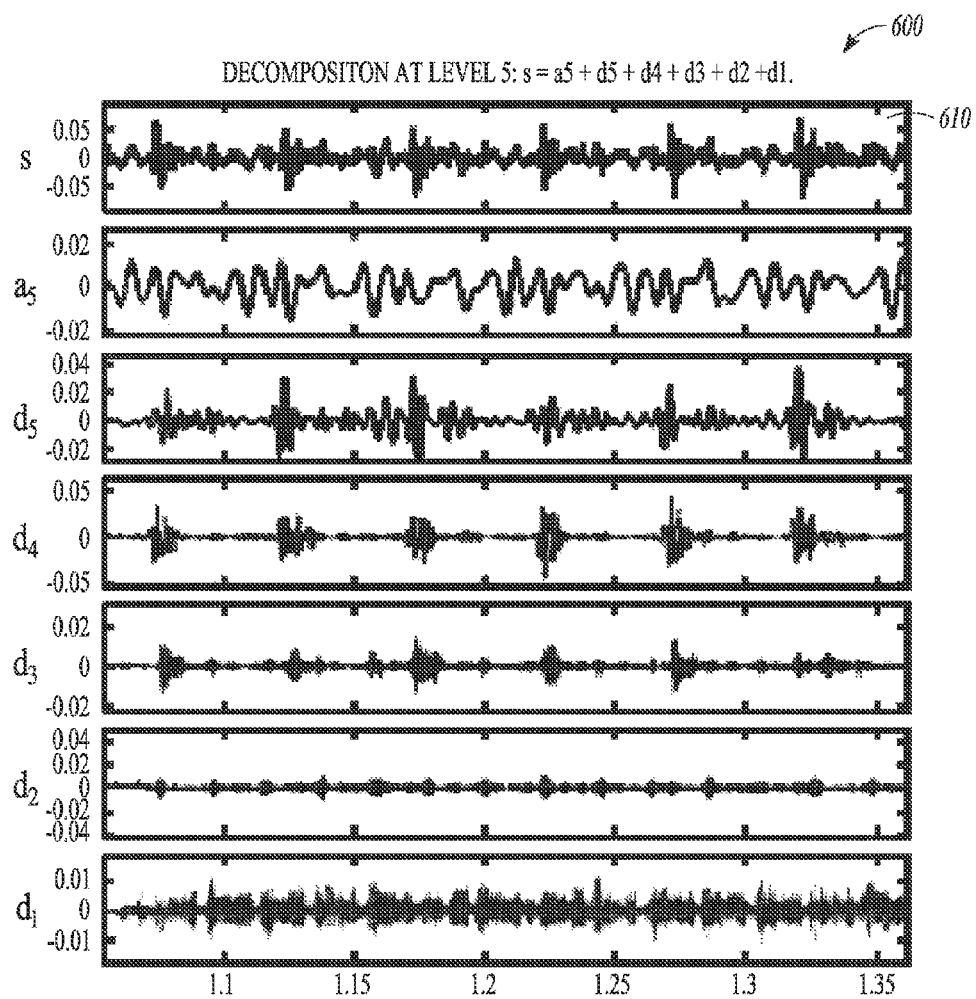
FIG. 6 shows graphical representations of the decomposition of the electrical signal obtained from a sensor.

Many different wavelet functions can be used to decompose the input electrical signal into component parts. In some examples, Daubechies wavelets are used. The ability of a wavelet function to decompose a signal into its component parts depends on how closely the wavelet used approximates the electrical signal. FIG. 6 shows graphical representations 600 of the decomposition of the electrical signal obtained from the sensor. A pre-compensated electrical signal 610 is shown in the top graph. In this example, the decomposition is performed by running the electrical signal through a bank of bandpass filters corresponding to the Daubechies wavelets to obtain the six individual decomposed element signals a5, d5, d4, d3, d2, and d1. In some examples, after the electrical signal 610 is decomposed into component signals, a filtered signal could be obtained by multiplying the decomposed signals by corresponding coefficients to weight the individual decomposed signals. Adding the weighted signals back together provides the filtered signal. A weighting coefficient of zero will eliminate a corresponding signal from the filtered signal result.

Figure 7:
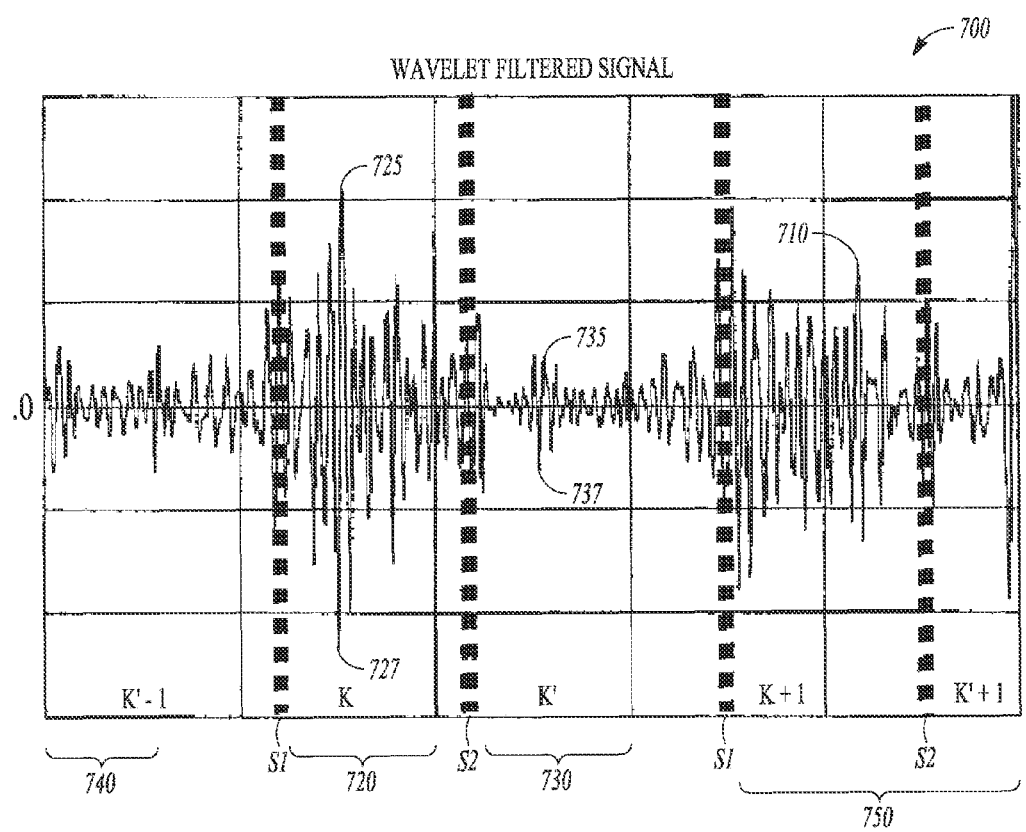
FIG. 7 shows a waveform of an electrical signal provided by a sensor that has been filtered by a wavelet filter.

FIG. 7 shows a waveform 700 of the wavelet filtered signal 710 output by the wavelet filter module 345 in FIGS. 3A-B in response to the pre-compensated signal 500 of FIG. 5. In certain examples, the VR calculation module 345 of FIGS. 3A-B is configured to calculate a measurement of VR for one or more heartbeats using signal intensity information of the wavelet filtered signal. The measurement typically includes a ratio of the energy of the electrical signal during systole 720 to the energy of the electrical signal during diastole 730. The energy of the electrical signal during systole typically is calculated by summing the samples during a heart contraction. The intensity in the signal during diastole is typically calculated by summing the samples during a heart expansion. This leads to the ratio VR metric:

$$\text{Ratio } VR \text{ Metric} = \frac{\sum_{i=1}^{m} |C_b(K+i)|}{\sum_{j=1}^{n} |C_b(K'+j)|}, \quad (1)$$

where K and K' are the beat index for systole and diastole respectively, m is the number of samples taken during systole, n is the number of samples taken during diastole, i and j are variables corresponding to the sample number, and $C_b$ corresponds to a measure of energy at that sample. An example of a measure of energy at a sample would be the amplitude of the signal. Another example would be the power of the signal.

In some examples, the ratio VR metric can be calculated on a per-beat basis. In FIG. 7, the ratio VR metric is calculated on the K,K' index beat by summing m samples taken during systole 720 and summing n samples taken during diastole 730. In some examples, n and m are the same integer number. For example, fifty samples could be collected during systole and fifty samples could be collected during diastole. Because the absolute value is used in equation 1, samples at signal peaks 725 and 727 are additive and result in a greater sum during systole 720 than a sum of samples including signal peaks 735 and 737 during diastole 730. In some examples, the resulting ratio VR metric is compared to a ratio VR metric threshold value and VR is declared when the measured ratio VR metric exceeds the ratio VR metric threshold value.

In some examples, the ratio VR metric is calculated over a specified number of beats. In an example where the ratio VR metric is calculated over three beats, in FIG. 7 the ratio VR metric is calculated over the K−1,K'−1 index beat 740 (partially shown), the K,K' index beat 720, 730, and the K+1,K'+1 index beat 750 (partially shown). In another example, the ratio VR metric is calculated over ten beats. In some examples, the total ratio VR metric calculated over the specified number of beats is compared to a ratio VR metric threshold value to declare VR. In some examples, a per-beat central tendency of the ratio VR metric calculated over the specified number of beats is compared to a ratio VR metric threshold value to declare VR.

Other VR metrics are possible. In an example, a measurement of VR includes the difference between the energy of the electrical signal during systole and the energy of the electrical signal during diastole. i.e., $$\text{Difference VR metric} = \sum_{i=1}^{m} |C_b(K+i)| - \sum_{j=1}^{n} |C_b(K'+j)|. \quad (2)$$

In some examples, the electrical signal provided by the sensor is used to identify or help identify systole and diastole. For example, the peak amplitude 405 of the accelerometer waveform of FIG. 4 indicates the start of systole. In some examples, one or more additional signals obtained by the system 300 are used to identify or help identify systole or diastole. In some examples, the system 300 further includes cardiac signal sensing circuits coupled to the controller circuit 320 and to electrodes located in association with the heart to detect one or more cardiac signals related to heart contractions. Cardiac signal artifacts such as P-waves (from atrial contractions) and R-waves (from ventricular contractions) are then correlated with the wavelet filtered signal to identify or help identify systole and diastole.

In some examples, heart sounds are additionally or alternatively correlated with the wavelet filtered signal to identify systole or diastole. Heart sounds are associated with mechanical vibrations from activity of a patient's heart and the flow of blood through the heart. Heart sounds recur with each cardiac cycle and are separated and classified according to the activity associated with the vibration. The first heart sound (S1 in FIG. 7) is the vibrational sound made by the heart during tensing of the mitral valve. The second heart sound (S2 in FIG. 7) marks the beginning of diastole. The heart sounds can be sensed using the same sensor that is used to detect VR or an additional sensor. Examples of sensors that can detect heart sounds include an accelerometer or a microphone.

The VR metric can be used to monitor VR for changes or incidents of VR. A wide variety of statistical methods can be used. In some embodiments, the controller circuit 320 of FIG. 3A-B merely keeps track of a count of VR events that exceed an VR metric threshold value. In some embodiments, the controller circuit 320 includes a central tendency computation module. The central tendency module calculates a central tendency of VR measurements, such as a running average for example, over a specified number of heartbeats.

In some examples, the systems 300 include memory circuits to store a trend or other information related to VR. In some examples, the system 300 includes a communication circuit coupled to the controller circuit 320 to wirelessly communicate information related to VR to an external device. In some examples, the external device contains the wavelet filter module or VR calculation module. The controller circuit 320 transmits to an external device sample values of the electrical signal obtained from the sensor or from a pre-compensated signal. The external device performs the wavelet filtering or the measurement of VR.

Figure 8:
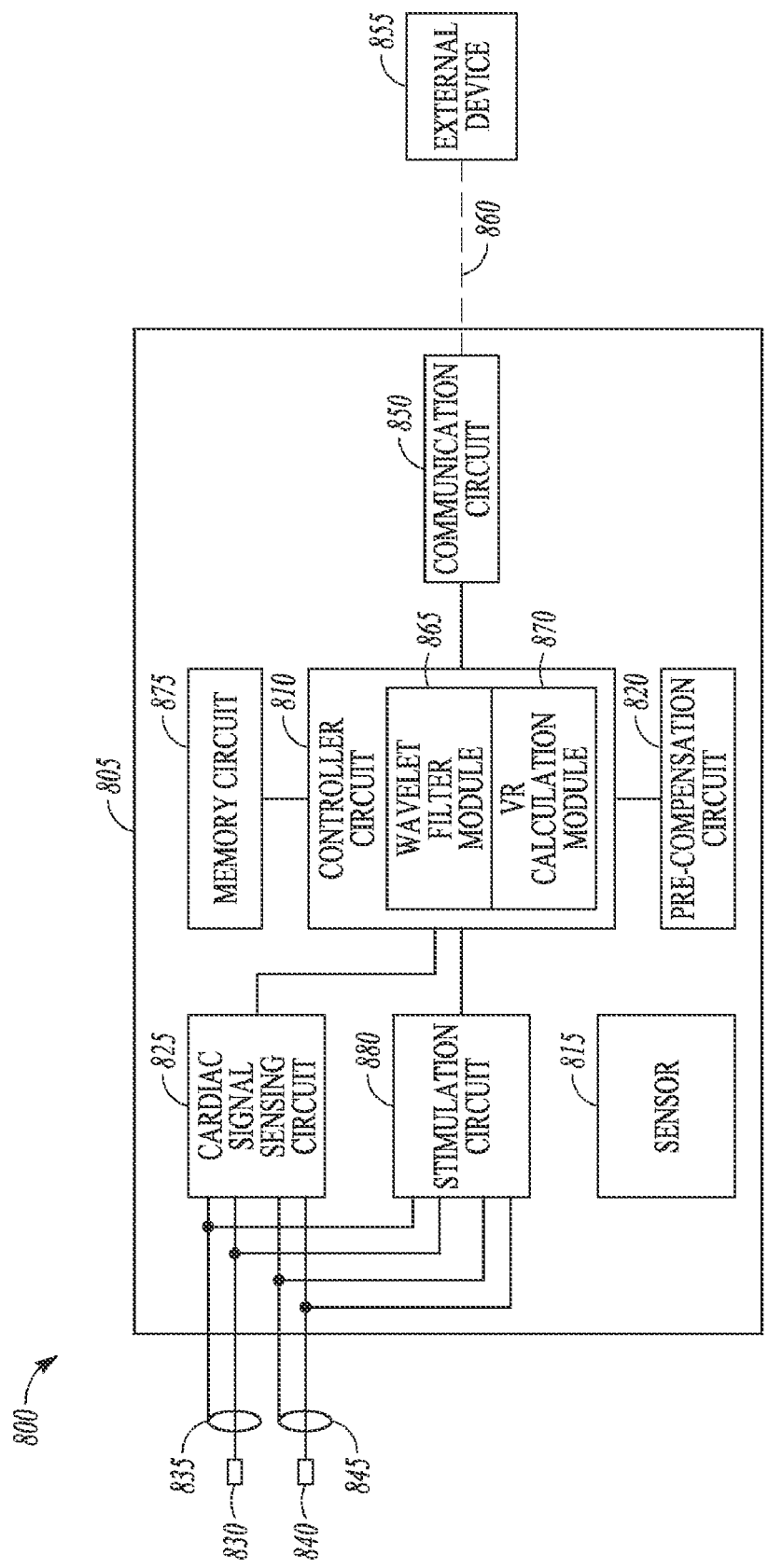
FIG. 8 shows an embodiment of portions of a system that detects VR using an implantable medical device.

FIG. 8 shows an embodiment of portions of a system 800 that detects VR using an IMD 805. The IMD 805 includes a controller circuit 810 and a sensor circuit 815. The sensor 815 produces an electrical signal representative of mechanical activity of a heart. In some examples, the sensor is within the IMD can. In some examples, the sensor includes its own hermetically sealed housing, is placed outside of the can of the IMD 805, and is connected to the IMD 805, such as by an implantable lead. In some examples, the sensor 815 includes an accelerometer. In some examples, the sensor 815 includes an implantable microphone. In some examples the sensor includes an implantable pressure sensor. The IMD 805 further includes a pre-compensation circuit 820 coupled between the controller circuit 810 and the sensor 815.

The IMD 805 further includes a cardiac signal sensing circuit 825 coupled to the controller circuit 810 and is configured to provide electrical signals representative of cardiac activity. In certain examples, the cardiac signal sensing circuit is coupled to one or more electrodes such as by one or more cardiac leads to tip electrodes 830, 840 and ring electrodes 835, 845. In some embodiments, the electrodes 830, 835 are configured to sense one or more cardiac signals of a right atrium and electrodes 840, 845 are configured to sense one or more cardiac signals of a right ventricle. In some embodiments, the electrodes 830, 835 are configured to sense one or more cardiac signals of a right ventricle and electrodes 840, 845 are configured to sense one or more cardiac signals of a left ventricle. The IMD 805 further includes a communication circuit 850 that communicates one or more wireless signals 860 with external device 855.

In some examples, the IMD 805 includes a wavelet filter module 865 and VR calculation module 870. The wavelet filter module 865 extracts signal energy information from the electrical signal output by the sensor 815, the energy information including variation of the signal amplitude with frequency and time. The VR calculation module 870 calculates a measurement of VR for one or more heartbeats using the energy information. Measurements of VR are stored in memory circuit 875. In certain examples, the VR measurement includes a ratio of energy of the electrical signal obtained from the sensor during systole to energy of the electrical signal obtained during diastole. The IMD 805 communicates information related to VR to the external device 855.

In some examples, the wavelet filter module 865 or VR calculation module 870 are included in the external device 855. The controller circuit 810 transmits the electrical signal obtained from the sensor 815 to the external device 855. The wavelet filtering or the calculation of the VR measurement is done in the external device 855. In some examples, the controller circuit 810 transmits a pre-compensated signal to the external device 855.

The IMD 805 further includes a stimulation circuit 880 coupled to the controller circuit 320 and cardiac electrodes. In some examples, the stimulation circuit 880 provides cardiac resynchronization therapy (CRT) to the heart. The controller circuit 810 initiates, terminates, or otherwise adjusts at least one stimulation parameter related to CRT, such as to reduce an amount of VR indicated by the measurement of VR, either alone or in combination with some other goal. In some examples, the cardiac leads and electrodes 830, 835, 840, 845 are configured to sense cardiac signals and provide CRT to the left and right ventricles. The controller circuit 810 is operable to adjust an interventricular delay between sensing or pacing a right ventricle and a left ventricle during the same cardiac cycle to reduce an amount of VR. In some examples, the cardiac leads and electrodes 830, 835, 840, 845 are configured to sense cardiac signals and provide pacing therapy to the atrium and ventricle. The controller circuit 810 is operable to adjust an A-V delay between pacing the atrium and the ventricle during the same cardiac cycle to reduce an amount of VR, either alone or in combination with some other goal. In some examples, the wavelet filter module 865 and VR calculation module 870 are included in the controller circuit 810 and controller circuit 810 calculates the adjustment to the stimulation parameter.

In some examples, the wavelet filter module 865 and VR calculation module 870 are included in the external device 855 and the external device 855 calculates the adjustment to the stimulation parameter and programs one or more parameters into the IMD 805. In some embodiments, the external device 855 is a local or remote IMD programmer and includes a display and presents one or more suggested stimulation parameters to a care giver who then optionally selects particular suggested parameters or selects different desired values for such parameters to be programmed into the IMD 805.

Figure 9:
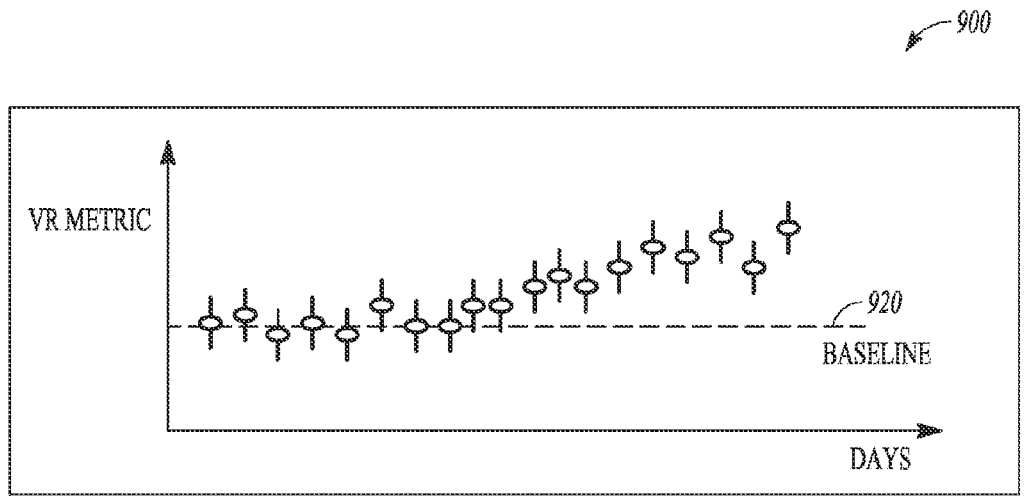
FIG. 9 shows a graph representing trending of VR data.

In some examples, the IMD 805 or the external device 855 uses VR information to trend VR for a patient. FIG. 9 shows a graph 900 representing trending of VR data by the external device 855. Data points 910 of VR measurements are used to calculate a baseline measurement value 920. If the data trending indicates an increase in the VR measurement (e.g., beyond a specified threshold), the external device 855 is operable to communicate an alarm indicating increased VR. This increase that causes an alarm to be indicated can be a sustained increase over time or a measurement that crosses a threshold VR value. In some examples, the alarm is a visual alarm on a display. In some examples, the alarm is an audible alarm. In some examples, the external device 855 is connected to a network and the alarm is indicated over the network. In some examples, the network includes a computer network such as a hospital network or the internet. In some examples the external device 855 is in communication with a server that is connected to a network. In some examples, the server includes memory, a processor, and a wavelet filter module and the VR calculation module. The server trends measurements of VR and the alarm indication originates from the server. In some examples, the network includes a mobile phone network. In some examples, the alarm is communicated from the IMD 805.

In certain examples, external device 855 provides an indication of heart failure (HF) decompensation. Because it is believed that VR increases with HF decompensation, the external device 855 uses the VR information to provide an indication of HF decompensation. In some examples, the indication of HF decompensation uses the information related to VR in addition to information related to at least one other measured physiologic parameter. Examples of these other measured physiologic parameters include intracardiac impedance, at least one heart sound, and patient respiration.

Figure 10:
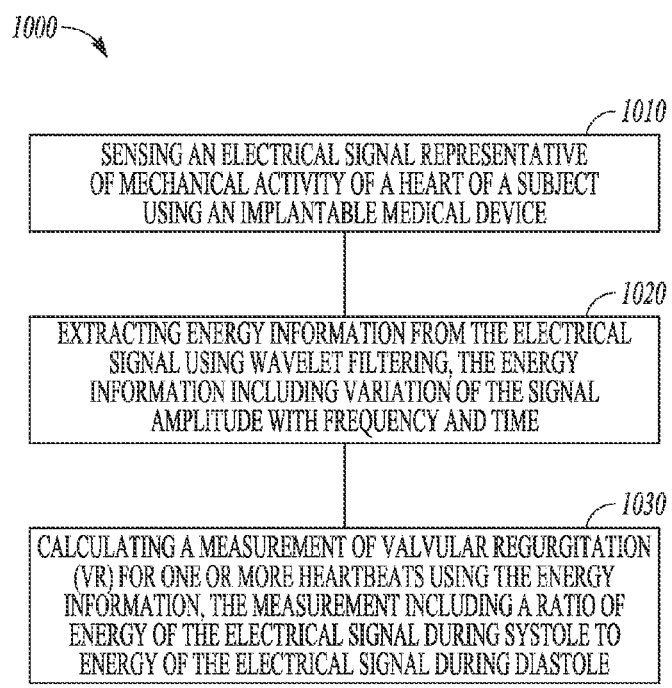
FIG. 10 shows a block diagram of an embodiment of a method of detecting VR.

FIG. 10 shows a block diagram of an embodiment of a method 1000 of detecting VR. At 1010, an electrical signal representative of mechanical heart activity of a subject is sensed using an implantable medical device (IMD). The electrical signal is provided by an implantable sensor that converts the mechanical activity into the electrical signal. Examples of such a sensor appropriate to sense mechanical activity related to VR include an accelerometer, a pressure sensor, and a microphone. For some sensors, the magnitude of the electrical signal provided rolls off with higher frequencies. In these cases, the method 1000 may further include compensating for this frequency response.

At 1020, energy information is extracted from the electrical signal using wavelet filtering. This energy information includes the variation of the signal amplitude with frequency and time. In some examples, the wavelet filtering uses Daubechies wavelets to decompose the electrical signal into its component signals. The component signals are multiplied by corresponding weighting coefficients to perform the filtering and are then recombined to obtain the wavelet filtered signal.

In some examples, wavelet filtering is done by a controller circuit, such as a processor, in the IMD. In some examples, a sampled electrical signal from the sensor, or a sampled electrical signal that has been pre-compensated, is communicated to an external device. In some examples, the external device then performs the wavelet filtering. An example of such an external device is an IMD programmer that communicates wirelessly with the IMD. In some examples, the external device transmits the sampled signal information to third device over a network and the third device performs the wavelet filtering. An example of such an external device is a computer in communication with a network and an example of the third device is a server. In another example, the external device is a repeater that communicates wirelessly with the IMD and with a third device in communication with a network, such as a computer network or mobile telephone network. The wavelet filtering can be performed by any device on the network that can receive the sampled signal information and contains a processor executing instructions to perform the wavelet filtering. An example of such a device is a server connected to the network.

At 1030, a measurement of VR is calculated for one or more heartbeats using the energy information. In certain examples, the VR measurement includes a ratio of the energy of the electrical signal during systole to the energy of the electrical signal during diastole. Typically it is more convenient for the device that performs the wavelet filtering (either an IMD or an external device) to also calculate the VR measurement from the wavelet filtered signal, but this is not strictly necessary. A digital representation of the wavelet filtered signal could be communicated to another device to calculate the VR measurement.

In some examples, an additional physiologic parameter is used to help identify systole and diastole in the wavelet filtered signal. Examples of the additional physiologic parameter include an electrogram (egram) of intrinsic electrical heart activity internally sensed, such as with the IMD, or heart sounds sensed with the IMD using the same or a different sensor used to provide the electrical signal representative of mechanical activity of a heart. In some examples, the method 1000 further includes calculating a central tendency of the measurement of VR over a predetermined number of beats.

Examples of a central tendency calculation include an average value and a median value of the VR measurement.

One cause of VR is dyssynchrony of contractions of the chambers of the heart. For this reason, some examples of the method 1000 include adjusting a stimulation parameter related to cardiac resynchronization therapy (CRT) to reduce an amount of VR indicated by the measurement of VR. An example of adjusting a stimulation parameter includes adjusting an A-V delay between sensing or pacing an atrium and pacing a ventricle during the same cardiac cycle in order to provide proper atrial-ventricular synchrony. Another example includes adjusting an interventricular delay between sensing or pacing a right ventricle (RV) and a left ventricle (LV) during the same cardiac cycle to provide proper RV-LV synchrony. Another example includes selecting a different vector or set of vectors to provide cardiac resynchronization therapy (CRT). The term "vector" refers to a combination of electrodes. If the electrodes are used to sense electrical signals, sensing among different sets of electrodes, or vectors, often provides directional information regarding the propagation of cardiac signals. Choosing a different vector to deliver therapy often provides a different area to deliver the therapy, a different direction to provide the therapy, or a different timing relationship among the possible combinations. The adjustment of the stimulating parameter can originate from the external device or the IMD. If adjustments to CRT parameters are made by the IMD based on VR calculations made by the IMD, the VR measurement and the CRT stimulation can form a closed loop feedback system such as to reduce or minimize VR in the heart.

It is desirable for a care giver to monitor changes in VR. For this reason, some examples of the method 1000 further include trending the measurement of VR over time. The trending can be done by either an IMD or an external device. A baseline VR measurement is calculated. Deviations from the baseline that are more than a specified threshold deviation cause the device to provide an indication of increased VR. An example of such an indication is an audible alarm provided by the IMD. Another example is a visual indication on a display provided by the external device. In some examples, the trending of the VR measurement over time is displayed on the external device. Trending is useful not only to monitor progress of VR but also to monitor how a patient responds to CRT. If one or more parameters related to CRT are changed, the responsiveness of the patient to the change can be measured by tracking the measurement of VR.

Because VR is believed to increase with HF decompensation, some examples of the method 1000 further include providing an indication of heart failure decompensation using the VR measurement. A sudden increase in VR indicated by the VR measurement can be caused by an HF decompensation event occurring or by a worsening condition of HF. In some examples, the VR measurement is combined with at least one other measured physiologic parameter to provide an indication of HF decompensation. This is useful if the VR measurement is needed to confirm HF decompensation indicated by the other measured physiologic parameter. Some examples of the other measured physiologic parameter include intracardiac impedance, amplitude of heart sounds, and patient respiration.

The systems and methods described herein may be used to detect other events related to cardiac activity in addition to VR, such as additional forms of heart murmurs. Use of a specific embodiment of the systems and methods may depend on particular placement of the sensor or sensors or may depend on the type of signature the cardiac event provides. For example, a specific type of cardiac event may be more readily detected and measured by using a different set of wavelets in the filtering.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations, or variations, or combinations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own.

What is claimed is:
1. A system comprising:
an implantable medical device (IMD) comprising:
an implantable sensor operable to produce an electrical signal representative of mechanical activity of a heart of a subject; and
a controller circuit coupled to the sensor, wherein the controller circuit includes:
a wavelet filter module including a wavelet filter, the wavelet filter module, configured to:
generate a set of time-frequency representations of the electrical signal; and
produce a wavelet filtered electrical signal using the set of time-frequency representations; and
a valvular regurgitation (VR) calculation module configured to calculate a measurement of VR for one or more heartbeats using a measurement of systolic energy of the wavelet filtered electrical signal during systole and a measurement of diastolic energy of the wavelet filtered electrical signal during diastole.

2. The system of claim 1, wherein the measurement of VR includes a ratio of energy of the electrical signal during systole to energy of the electrical signal during diastole.

3. The system of claim 1, wherein the measurement of VR includes a difference of energy of the electrical signal during systole to energy of the electrical signal during diastole.

4. The system of claim 1, further including a pre-compensation circuit coupled to the sensor and the controller circuit, the pre-compensation circuit including a frequency response to compensate for the frequency response of the sensor.

5. The system of claim 1, wherein the controller circuit further includes a central tendency computation module to calculate a central tendency of VR measurements over a specified number of heartbeats.

6. The system of claim 1, wherein the IMD further includes a stimulation circuit coupled to the controller circuit, the stimulation circuit to provide cardiac resynchronization therapy (CRT) to the heart, and wherein the controller circuit is operable to adjust at least one stimulation parameter related to CRT to reduce an amount of VR indicated by the measurement of VR.

7. The system of claim 6, wherein the controller circuit is operable to adjust an A-V delay between pacing an atrium and a ventricle during the same cardiac cycle to reduce an amount of VR.

8. The system of claim 6, wherein the controller circuit is operable to adjust an interventricular delay between pacing a right ventricle and a left ventricle during the same cardiac cycle to reduce an amount of VR.

9. The system of claim 1, wherein the IMD further includes a communication circuit coupled to the controller circuit, and wherein the system further includes an external device operable to communicate with the IMD to obtain information related to VR.

10. The system of claim 9, wherein the external device is in communication with a network.

11. The system of claim 9, wherein the external device is operable to communicate an alarm indicating increasing VR.

12. The system of claim 9, wherein the external device includes an indication of heart failure (HF) decompensation that uses the information related to VR.

13. The system of claim 12, wherein the indication of HF decompensation uses the information related to VR in addition to information related to at least one other measured physiologic parameter.

14. The system of claim 13, wherein the physiologic parameter is selected from the group consisting of:
intracardiac impedance;
at least one heart sound; and
patient respiration.

15. The system of claim 1, wherein the implantable sensor includes an implantable accelerometer.

16. The system of claim 1, wherein the implantable sensor includes an implantable pressure sensor.

17. The system of claim 1, wherein the implantable sensor includes an implantable microphone.

18. A system comprising:
an implantable medical device (IMD) comprising:
an implantable sensor operable to produce an electrical signal representative of mechanical activity of a heart of a subject;
a sampling circuit coupled to the sensor circuit to produce digital representations of the electrical signal;
a communication circuit; and
a controller circuit coupled to the communication circuit and the sampling circuit, the controller circuit operable to communicate the digital representations; and
an external device comprising:
a communication circuit operable to communicate information with the IMD, the information including the digital representations;
a processor coupled to the communication circuit, the processor including:
a wavelet filter module including a wavelet filter, the wavelet filter module configured to:
generate a set of time-frequency representations of the electrical signal; and
produce a wavelet filtered electrical signal using the set of time-frequency representations; and
a valvular regurgitation (VR) module configured to calculate a measurement of VR for one or more heartbeats using a ratio of a measurement of systolic energy of the wavelet filtered electrical signal during systole to a measurement of diastolic energy of the wavelet filtered electrical signal during diastole.

19. The system of claim 18, wherein the external device includes an IMD programmer and the IMD further includes a stimulation circuit coupled to the controller circuit, the stimulation circuit to provide cardiac resynchronization therapy (CRT) to the heart, and wherein the IMD programmer is operable to adjust at least one stimulation parameter in the IMD related to CRT to reduce an amount of VR indicated by the measurement of VR.

20. The system of claim 19, wherein the IMD programmer is operable to adjust an A-V delay between pacing an atrium and a ventricle during the same cardiac cycle to reduce an amount of VR.

21. The system of claim 19, wherein the IMD programmer is operable to adjust an interventricular delay between pacing a right ventricle and a left ventricle during the same cardiac cycle to reduce an amount of VR.

22. The system of claim 18, wherein the external device is in communication with a server, the server connected to a network, the server including memory, the server operable to trend measurements of VR.

23. The system of claim 22, wherein the server includes an indication of heart failure (HF) decompensation that uses the information related to VR.

24. The system of claim 23, wherein the indication of HF decompensation uses the information related to VR in addition to information related to at least one other measured physiologic parameter to provide an indication of heart failure decompensation, wherein the physiologic parameter is selected from the group consisting of:
intracardiac impedance;
amplitude of at least one heart sound; and
patient respiration.

25. The system of claim 22, wherein the server is operable to provide an alarm indicating heart failure decompensation.

26. A method comprising:
sensing an electrical signal representative of mechanical activity of a heart of a subject using an implantable medical device;
generating a set of time-frequency representations of the electrical signal
producing a wavelet filtered electrical signal using the set of time-frequency representations; and
calculating a measurement of valvular regurgitation (VR) for one or more heartbeats using a ratio of a measurement of systolic energy of the wavelet filtered electrical signal during systole to a measurement of diastolic energy of the wavelet filtered electrical signal during diastole.

27. The method of claim 26, wherein obtaining an electrical signal includes compensating for a sensing frequency response.

28. The method of claim 26, further including calculating a central tendency of the measurement of VR over a predetermined number of beats.

29. The method of claim 26, wherein the method further includes adjusting a stimulation parameter related to cardiac resynchronization therapy (CRT) to reduce an amount of VR indicated by the measurement of VR.

30. The method of claim 29, wherein adjusting a stimulation parameter related to CRT includes adjusting an A-V delay between pacing an atrium and a ventricle during the same cardiac cycle.

31. The method of claim 29, wherein adjusting a pacing parameter related to CRT includes adjusting an interventricular delay between pacing a right ventricle and a left ventricle during the same cardiac cycle.

32. The method of claim 26, further including trending the measurement of VR and displaying the trending over time.

33. The method of claim 26, further including providing an indication of heart failure decompensation using the VR measurement.

34. The method of claim 33, wherein providing an indication of heart failure decompensation using the VR measurement includes using the VR measurement in combination with at least one other measured physiologic parameter.

35. The method of claim 34, wherein the measured physiologic parameter is selected from the group consisting of:
   intracardiac impedance;
   amplitude of heart sounds; and
   patient respiration.

* * * * *